(12) United States Patent
Youssef et al.

(10) Patent No.: US 11,972,848 B1
(45) Date of Patent: Apr. 30, 2024

(54) SYSTEM AND METHOD OF FACILITATING MEDICAL APPOINTMENT RECORD CREATION WITH A MINIMUM OF USER INPUT ACTIONS

(71) Applicant: TapType Limited, Dublin (IE)

(72) Inventors: Victor Youssef, Oakville (CA); Malak Francis, Cairo (EG); Ingy Anees, Cairo (EG)

(73) Assignee: TapType Limited, Dublin (IE)

( * ) Notice: Subject to any disclaimer, the term of this patent is extended or adjusted under 35 U.S.C. 154(b) by 0 days.

(21) Appl. No.: 18/131,510

(22) Filed: Apr. 6, 2023

(30) Foreign Application Priority Data

Sep. 17, 2022 (CA) ..................... 3174732

(51) Int. Cl.
*G06F 3/0484* (2022.01)
*G06F 3/04886* (2022.01)
*G16H 10/60* (2018.01)

(52) U.S. Cl.
CPC ........... *G16H 10/60* (2018.01); *G06F 3/0484* (2013.01); *G06F 3/04886* (2013.01)

(58) Field of Classification Search
None
See application file for complete search history.

(56) References Cited

U.S. PATENT DOCUMENTS

| 7,716,072 | B1 | 5/2010 | Green, Jr. et al. |
| 2009/0062623 | A1 | 3/2009 | Cohen et al. |
| 2009/0125322 | A9 | 5/2009 | Dahlin et al. |
| 2010/0131482 | A1 | 5/2010 | Linthicum et al. |
| 2012/0022892 | A1 | 1/2012 | Feldman et al. |
| 2012/0059671 | A1 | 3/2012 | Park et al. |
| 2013/0030836 | A1* | 1/2013 | Ackerson ............... G16H 10/20 705/3 |
| 2015/0317436 | A1* | 11/2015 | Kutty ..................... G16H 50/20 705/3 |
| 2016/0283676 | A1 | 9/2016 | Lyon et al. |
| 2018/0301222 | A1 | 10/2018 | Dew, Sr. et al. |

(Continued)

OTHER PUBLICATIONS

Alyssa Klein; Leah Kulp; Aleksandra Sarcevic, Designing and Optimizing Digital Applications for Medical Emergencies, Apr. 30, 2018.

*Primary Examiner* — Rinna Yi

(57) ABSTRACT

To facilitate generating a record of a medical appointment with minimal user input actions, a plurality of user-selectable GUI elements indicating a respective plurality of medical case types is displayed. Responsive to a user selection indicating a type of medical case, a medical case-specific plurality of GUI question elements is dynamically displayed within a first user-selectable GUI region, each including an indicator of a subjective question regarding a condition of a patient presenting with the indicated medical case type and multiple user-selectable GUI response elements indicating multiple respective distinct patient responses to the subjective question. Within a second user-selectable GUI region, a medical case-specific plurality of GUI prompt elements is dynamically displayed, each including an indicator of a prompt to perform an objective observation of the patient presenting with the indicated medical case type and multiple user-selectable GUI input elements indicating multiple respective distinct outcomes to the prompted objective observation.

20 Claims, 18 Drawing Sheets

(56) References Cited

U.S. PATENT DOCUMENTS

| | | |
|---|---|---|
| 2018/0349556 A1 | 12/2018 | Owen |
| 2019/0325726 A1* | 10/2019 | Clawson ................ G16H 10/60 |
| 2021/0098086 A1 | 4/2021 | Hussam |
| 2022/0013234 A1 | 1/2022 | Feldman et al. |
| 2022/0051805 A1 | 2/2022 | Yerebakan et al. |
| 2022/0223291 A1* | 7/2022 | Moen .................... G16H 15/00 |

* cited by examiner

SYSTEM AND METHOD OF FACILITATING MEDICAL APPOINTMENT RECORD CREATION WITH A MINIMUM OF USER INPUT ACTIONS

TECHNICAL FIELD

The present disclosure relates to a system and method of facilitating medical appointment record creation with a minimum of user input actions.

BACKGROUND

During a medical appointment, a doctor may examine a patient who presents with one or more medical cases. In this document, the term "medical case," or simply "case," refers to a particular instance of a disease or other medical problem. Examples of a medical case include a headache, vomiting, dizziness, chicken pox, a sprain, and the like.

The doctor may wish to make a record of what transpired during the appointment. Historically, such record-keeping was performed manually, e.g., using a pen and paper. More recently, doctors may be more inclined to use a computer to keep notes electronically. In the case of electronic notes, data entry may be performed using a conventional alphanumeric keyboard. Keyboard-based data entry may be tedious, slow, and prone to error.

SUMMARY

In one aspect, there is provided a computer-implemented method comprising: displaying, by a computing device, a plurality of user-selectable graphical user interface (GUI) elements, each of the user-selectable GUI elements indicating a respective type of medical case; responsive to a user selection of one of the GUI elements, the user selection resulting in an indicated type of medical case: dynamically displaying, by the computing device, within a first user-selectable GUI region, a medical case-specific plurality of GUI question elements, each of the GUI question elements including: an indicator of a subjective question regarding a condition of a patient presenting with the indicated type of medical case; and a plurality of user-selectable GUI response elements indicating a respective plurality of distinct patient responses to the subjective question; and dynamically displaying, by the computing device, within a second user-selectable GUI region independently user-selectable from the first user-selectable GUI region, a medical case-specific plurality of GUI prompt elements, each of the GUI prompt elements including: an indicator of a prompt to perform an objective observation of the patient presenting with the indicated type of medical case; and a plurality of user-selectable GUI input elements indicating a respective plurality of distinct outcomes to the prompted objective observation.

In some embodiments, the plurality of user-selectable GUI elements is a first plurality of user-selectable GUI elements and the method further comprises: further displaying, by the computing device, a second plurality of user-selectable GUI elements, each of the user-selectable GUI elements of the second plurality indicating a respective body system; responsive to a user selection of one of the GUI elements of the second plurality, the user selection resulting in an indicated body system: further dynamically displaying, by the computing device, within the first user-selectable GUI region, a body system-specific plurality of further GUI question elements, each of the further GUI question elements including: an indicator of a further subjective question regarding a condition of the patient pertaining to the indicated body system; and a further plurality of user-selectable GUI response elements indicating a respective plurality of distinct patient responses to the further subjective question; and further dynamically displaying, by the computing device, within the second user-selectable GUI region, a body system-specific plurality of further GUI prompt elements, each of the further GUI prompt elements including: an indicator of a further prompt to perform an objective observation of the patient pertaining to the indicated body system; and a further plurality of user-selectable GUI input elements indicating a respective further plurality of distinct outcomes to the objective observation prompted by the further prompt.

In some embodiments, the method further comprises: further displaying, by the computing device, a plurality of user-selectable additional subjective questions regarding the condition of the patient, the user-selectable additional subjective questions being grouped by body system; responsive to a user selection of one of the additional subjective questions, the user selection resulting in a selected additional subjective question regarding the condition of the patient, further dynamically displaying, by the computing device, within the first user-selectable GUI region, an additional GUI question element including: an indicator of the selected additional subjective question regarding the condition of the patient; and an associated plurality of user-selectable GUI response elements indicating an associated respective plurality of distinct patient responses to the selected additional subjective question.

In some embodiments, the method further comprises: further displaying, by the computing device, a plurality of user-selectable additional prompts to make respective objective observations of the patient, the user-selectable additional prompts being grouped by body system; responsive to a user selection of one of the additional prompts, the user selection resulting in a selected additional prompt to make an objective observation of the patient, further dynamically displaying, by the computing device, within the second user-selectable GUI region, an additional GUI prompt element including: an indicator of the selected additional prompt to make the objective observation of the patient; and an associated plurality of user-selectable GUI input elements indicating an associated respective plurality of distinct outcomes to the objective observation of the patient prompted by the selected additional prompt.

In some embodiments, the method further comprises receiving a user selection of one of the first user-selectable GUI region and the second user-selectable GUI region and, responsive thereto, causing, by the computing device, the selected one of the first user-selectable GUI region and the second user-selectable GUI region to at least partially overlay the other of the first user-selectable GUI region and the second user-selectable GUI region.

In some embodiments, the computing device comprises a touchscreen and each of the GUI elements, each of the GUI response elements, each of the GUI input elements, the first GUI region, and the second GUI region are each individually user-selectable by a respective tap input of the touchscreen.

In another aspect, there is provided a system comprising: a computing device including: at least one processor; and non-transitory memory, communicatively coupled to the at least one processor, storing instructions that, upon execution by the at least one processor, cause the computing device to: display a plurality of user-selectable graphical user interface (GUI) elements, each of the user-selectable GUI elements indicating a respective type of medical case; responsive to a user selection of one of the GUI elements, the user selection resulting in an indicated type of medical case: dynamically display, within a first user-selectable GUI region, a medical case-specific plurality of GUI question elements, each of the GUI question elements including: an indicator of a subjective question regarding a condition of a patient presenting with the indicated type of medical case; and a plurality of user-selectable GUI response elements indicating a respective plurality of distinct patient responses to the subjective question; and dynamically display, within a second user-selectable GUI region independently user-selectable from the first user-selectable GUI region, a medical case-specific plurality of GUI prompt elements, each of the GUI prompt elements including: an indicator of a prompt to perform an objective observation of the patient presenting with the indicated type of medical case; and a plurality of user-selectable GUI input elements indicating a respective plurality of distinct outcomes to the prompted objective observation.

In some embodiments, the plurality of user-selectable GUI elements is a first plurality of user-selectable GUI elements and the instructions further cause the computing device to: further display a second plurality of user-selectable GUI elements, each of the user-selectable GUI elements of the second plurality indicating a respective body system; responsive to a user selection of one of the GUI elements of the second plurality, the user selection resulting in an indicated body system: further dynamically display, within the first user-selectable GUI region, a body system-specific plurality of further GUI question elements, each of the further GUI question elements including: an indicator of a further subjective question regarding a condition of the patient pertaining to the indicated body system; and a further plurality of user-selectable GUI response elements indicating a respective plurality of distinct patient responses to the further subjective question; and further dynamically display, within the second user-selectable GUI region, a body system-specific plurality of further GUI prompt elements, each of the further GUI prompt elements including: an indicator of a further prompt to perform an objective observation of the patient pertaining to the indicated body system; and a further plurality of user-selectable GUI input elements indicating a respective further plurality of distinct outcomes to the objective observation prompted by the further prompt.

In some embodiments, the instructions further cause the computing device to: further display a plurality of user-selectable additional subjective questions regarding the condition of the patient, the user-selectable additional subjective questions being grouped by body system; responsive to a user selection of one of the additional subjective questions, the user selection resulting in a selected additional subjective question regarding the condition of the patient, further dynamically display, within the first user-selectable GUI region, an additional GUI question element including: an indicator of the selected additional subjective question regarding the condition of the patient; and an associated plurality of user-selectable GUI response elements indicating an associated respective plurality of distinct patient responses to the selected additional subjective question.

In some embodiments, the instructions further cause the computing device to: further display a plurality of user-selectable additional prompts to make respective objective observations of the patient, the user-selectable additional prompts being grouped by body system; responsive to a user selection of one of the additional prompts, the user selection resulting in a selected additional prompt to make an objective observation of the patient, further dynamically display, within the second user-selectable GUI region, an additional GUI prompt element including: an indicator of the selected additional prompt to make the objective observation of the patient; and an associated plurality of user-selectable GUI input elements indicating an associated respective plurality of distinct outcomes to the objective observation of the patient prompted by the selected additional prompt.

In some embodiments, the instructions further cause the computing device to receive a user selection of one of the first user-selectable GUI region and the second user-selectable GUI region and, responsive thereto, cause the selected one of the first user-selectable GUI region and the second user-selectable GUI region to at least partially overlay the other of the first user-selectable GUI region and the second user-selectable GUI region.

In some embodiments, the computing device comprises a touchscreen and the instructions cause each of the GUI elements, each of the GUI response elements, each of the GUI input elements, the first GUI region, and the second GUI region to be individually user-selectable by a respective tap input of the touchscreen.

In another aspect, there is provided a non-transitory machine-readable medium storing instructions that, when executed by one or more processors of a computing device, cause the computing device to: display, on a display of the computing device, a plurality of user-selectable graphical user interface (GUI) elements, each of the user-selectable GUI elements indicating a respective type of medical case; responsive to a user selection of one of the GUI elements, the user selection resulting in an indicated type of medical case: dynamically display, on the display of the computing device, within a first user-selectable GUI region, a medical case-specific plurality of GUI question elements, each of the GUI question elements including: an indicator of a subjective question regarding a condition of a patient presenting with the indicated type of medical case; and a plurality of user-selectable GUI response elements indicating a respective plurality of distinct patient responses to the subjective question; and dynamically display, on the display of the computing device, within a second user-selectable GUI region independently user-selectable from the first user-selectable GUI region, a medical case-specific plurality of GUI prompt elements, each of the GUI prompt elements including: an indicator of a prompt to perform an objective observation of the patient presenting with the indicated type of medical case; and a plurality of user-selectable GUI input elements indicating a respective plurality of distinct outcomes to the prompted objective observation.

In some embodiments, the plurality of user-selectable GUI elements is a first plurality of user-selectable GUI elements and the instructions further cause the computing device to: further display, on the display of the computing device, a second plurality of user-selectable GUI elements, each of the user-selectable GUI elements of the second plurality indicating a respective body system; responsive to a user selection of one of the GUI elements of the second plurality, the user selection resulting in an indicated body system: further dynamically display, on the display of the computing device, within the first user-selectable GUI region, a body system-specific plurality of further GUI question elements, each of the further GUI question elements including: an indicator of a further subjective question regarding a condition of the patient pertaining to the indicated body system; and a further plurality of user-selectable GUI response elements indicating a respective plurality of distinct patient responses to the further subjective question;

and further dynamically display, on the display of the computing device, within the second user-selectable GUI region, a body system-specific plurality of further GUI prompt elements, each of the further GUI prompt elements including: an indicator of a further prompt to perform an objective observation of the patient pertaining to the indicated body system; and a further plurality of user-selectable GUI input elements indicating a respective further plurality of distinct outcomes to the objective observation prompted by the further prompt.

In some embodiments, the instructions further cause the computing device to: further display, on the display of the computing device, a plurality of user-selectable additional subjective questions regarding the condition of the patient, the user-selectable additional subjective questions being grouped by body system; responsive to a user selection of one of the additional subjective questions, the user selection resulting in a selected additional subjective question regarding the condition of the patient, further dynamically display, on the display of the computing device, within the first user-selectable GUI region, an additional GUI question element including: an indicator of the selected additional subjective question regarding the condition of the patient; and an associated plurality of user-selectable GUI response elements indicating an associated respective plurality of distinct patient responses to the selected additional subjective question.

In some embodiments, the instructions further cause the computing device to: further display, on the display of the computing device, a plurality of user-selectable additional prompts to make respective objective observations of the patient, the user-selectable additional prompts being grouped by body system; responsive to a user selection of one of the additional prompts, the user selection resulting in a selected additional prompt to make an objective observation of the patient, further dynamically display, on the display of the computing device, within the second user-selectable GUI region, an additional GUI prompt element including: an indicator of the selected additional prompt to make the objective observation of the patient; and an associated plurality of user-selectable GUI input elements indicating an associated respective plurality of distinct outcomes to the objective observation of the patient prompted by the selected additional prompt.

In some embodiments, the instructions further cause the computing device to receive a user selection of one of the first user-selectable GUI region and the second user-selectable GUI region and, responsive thereto, cause the selected one of the first user-selectable GUI region and the second user-selectable GUI region to at least partially overlay the other of the first user-selectable GUI region and the second user-selectable GUI region.

In some embodiments, the computing device comprises a touchscreen and the instructions cause each of the GUI elements, each of the GUI response elements, each of the GUI input elements, the first GUI region, and the second GUI region to be individually user-selectable by a respective tap input of the touchscreen.

BRIEF DESCRIPTION OF THE DRAWINGS

In the figures which illustrate example embodiments.

DESCRIPTION

In this document, any use of the term "exemplary" should be understood to mean "an example of" and not necessarily to mean that the example is preferable or optimal in some way. Any use of the term "doctor" should be understood to include any suitably qualified medical professional. Terms such as "below" may be used to describe a position or orientation of certain features of some embodiments, e.g., relative to other features, but should not be understood to connote a required orientation of the embodiments during manufacture or use.

Figure 1:
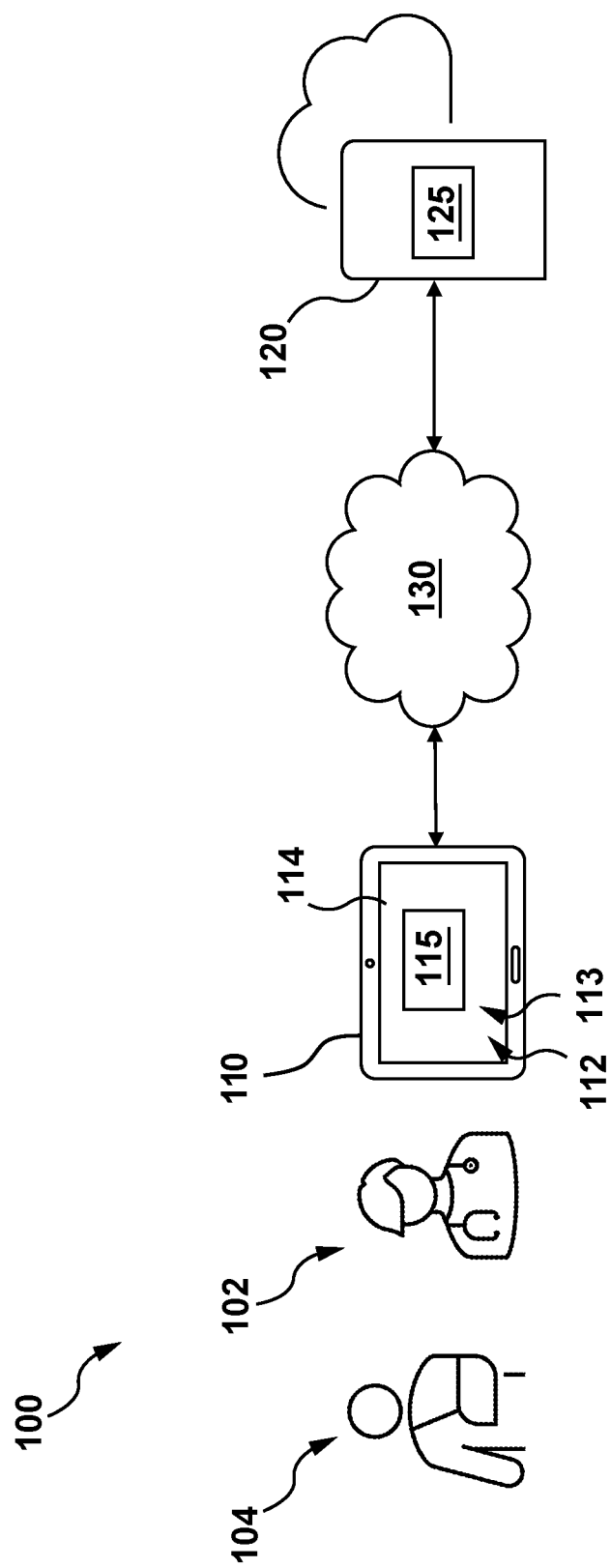
FIG. 1 is a schematic diagram of a system that facilitates medical appointment record creation with a minimum of user input actions.

FIG. 1 is a schematic diagram of a system 100 for facilitating medical appointment record creation with a minimum of user input actions. The system 100 may be used by a doctor 102 (or other user) to efficiently and quickly generate a thorough record of a medical appointment either during the appointment or soon afterwards. To that end, the system may enable the user to easily dynamically construct or populate a graphical user interface (GUI) that is highly patient-specific and appointment-specific and to immediately use the GUI to facilitate generating a record of the medical appointment with a minimum of user input actions.

In overview, the system 100 may minimize the number of user input actions required to generate a record of a medical appointment by implementing a "multi-granular" dynamic GUI construction approach. In this approach, the system maintains a database representing the universe (pool) of questions that may be asked by a doctor in a medical appointment setting. The pool includes both questions regarding subjective conditions of the patient (e.g., "Have you been sleeping well?") and prompts (which may also be questions) for the doctor to make objective observations of the patient (e.g., "Respiratory rate?"). For each question and each prompt, the database also stores an associated set of user-selectable responses (e.g., "Yes", "No", "Normal", "Irregular", etc.).

Within the pool, the questions and prompts are grouped into multiple, possibly overlapping groups (sets) of questions/prompts based on common grouping criteria. A first grouping criterion may be relevance to a common medical case. For example, a "chicken pox" group may encompass multiple questions regarding subjective conditions of a patient presenting with chicken pox as well as multiple prompts for the doctor to make suitable objective observations of a patient presenting with chicken pox as part of generating a complete record of a medical appointment with such a patient. Similarly, a "vomiting" group of questions/prompts may encompass multiple questions/prompts to be answered/followed to facilitate recording a medical appointment with a patient who presents with a case of vomiting.

A second grouping criterion may be relevance to a particular body system, i.e., physiological system of the human body (e.g., pulmonary, nervous, etc.) that may alternatively referred to simply as a "system." For example, a "Cardiology" group of questions/prompts may encompass multiple questions/prompts for assessing a patient's cardiological system during a medical appointment. Similarly, all of the questions/prompts for assessing a patient's neurological system may be categorized into a "neurology" group.

The system presents a user interface in which user selection of a group of questions/prompts populates the GUI with all of the questions/prompts of the group at once. This may be achieved with minimal user input action(s), e.g., by the click of a button representing the relevant group. A GUI may thus be quickly populated with possibly large groups of relevant questions/prompts, group by group, i.e., in a "coarse-grained" manner. If required, questions/prompts may also be added to the GUI in a "fine-grained" manner, i.e., individually.

The GUI defines two user-selectable GUI regions, such as tabs. The aforementioned questions and prompts are populated into the first and second GUI regions, respectively. More specifically, the first GUI region will contain GUI question elements including subjective questions regarding a condition of a patient and multiple predetermined user-selectable responses for each question (e.g., using a multiple-choice type format). The second GUI region will contain GUI prompt elements including prompts to make objective observations of the patient and multiple predetermined user-selectable responses indicating respective outcomes of the observation. Selection of one of the GUI regions may cause it to become a focus of the GUI. A GUI region may be considered to be a "focus" of the GUI when data entry can be performed within the GUI region via a user input mechanism of a device (e.g., a touchscreen or pointing device) displaying the GUI region. The data entry may for example be performed by interacting with GUI constructs within the GUI region (e.g., by tapping them on a touchscreen or clicking them with a pointing device). A user may be able to straightforwardly interact with the content of the first GUI region, select the second GUI region (which may cause it to at least partially overlay the first GUI region), and then interact with the content of the second GUI region.

Collectively, the coarse-grained and fine-grained construction approach permits a highly customized patient-specific and appointment-specific GUI to be dynamically constructed with a minimum of user input actions. The dynamically constructed GUI may be immediately useable to generate a record of a medical appointment in real time, also with a minimum of user input actions.

To the extent that any questions and/or prompts overlap between groups, any redundancy as between the questions may be removed as the GUI is dynamically constructed. This may promote GUI compactness, which may in turn promote efficiency of a computing device on which the GUI is displayed. For example, if a "Headache" medical case group and a "Neurology" body system group both contain the same question, e.g., regarding sensitivity to light, and if the "Headache" group of questions/prompts and the "Neurology" group of questions/prompts were both added to the same GUI region, the system may detect the redundancy and avoid populating the form with a second instance of the redundant question.

Use of the system 100 may require little or no technological expertise pertaining to GUI creation. In some embodiments, a doctor 102 may dynamically create a patient-specific GUI, as well as answer all of the questions and respond to all of the prompts in the dynamically created GUI, simply by tapping on a touchscreen of a portable computing device 120. In at least some embodiments, typing on a keyboard may be entirely avoided. As a result, the number of user input actions required to document the medical appointment may be minimized, and the speed and accuracy of record generation may be improved.

Referring to FIG. 1, the example system 100 includes a local computing device 110 and a server 120 communicatively coupled by a network 130, such as the internet.

The computing device 110 may be a portable computing device, such as a tablet, smartphone, or laptop computer. The computing device 110 may be referred to as a "local" device with respect to a user (e.g., doctor 102), who may use the device in a clinical setting (e.g., a doctor's office) in which a medical appointment may be conducted. The computing device 110 has at least one processor 112 communicatively coupled with non-transitory memory 113 and a display 114. In some embodiments, the display 114 comprises a touchscreen.

The memory 113 may be volatile memory, non-volatile memory, or a combination of these. To facilitate connection to the network 130, the computing device 110 may further include a network interface controller or network adapter (not illustrated). Alternatively, or in conjunction, the computing device may include suitable antennas, transceivers, and software (not illustrated) for wireless communication, e.g., conforming to Wi-Fi™ standard(s) such as IEEE 802.11 a/b/g/n/ac/ax.

In the embodiment depicted in FIG. 1, the memory 113 stores a browser application 115 (or simply "browser"), such as Google® Chrome™, executable by the computing device 110. The browser 115 may be capable of browsing web content written in Hyper Text Markup Language (HTML), template language, JavaScript, or other languages or formats. As will be appreciated, the browser 115 may be used to invoke and interact with a web-based application 125 hosted at server 120, which may facilitate the functionality described herein.

The server 120 may for example be a cloud-based web server or cloud computing platform, such as Amazon® Web Services™. The server 120 comprises hardware and software that serves web content responsive to requests received via the HyperText Transfer Protocol (HTTP) or HyperText Transfer Protocol Secure (HTTPS) protocols. It will be appreciate that the server 120 is a form of computing device.

The application 125 may be a web application accessible via a predetermined Uniform Resource Locator (URL). In some embodiments, the web application 125 may be a single-page application. As will be appreciated, a single-page application is a form of web application operable to dynamically rewrite a web page with new data, e.g., in response to user actions, rather than causing new web pages to be loaded. The single-page application may be used to present a dynamically changeable GUI in a browser 115 whose look and feel may be generally consistent regardless of the browser by which the web application 125 is accessed. Use of a single-page application implementation may avoid the need to install a dedicated client software application at the computing device 110 to access the functionality described herein. Instead, the web application 125 may be executable from any internet-connected device running a contemporary browser. The single-page application may for example be written in one or more software programming languages such as PHP: Hypertext Preprocessor (PHP), HTML, and JavaScript.

Figure 2:
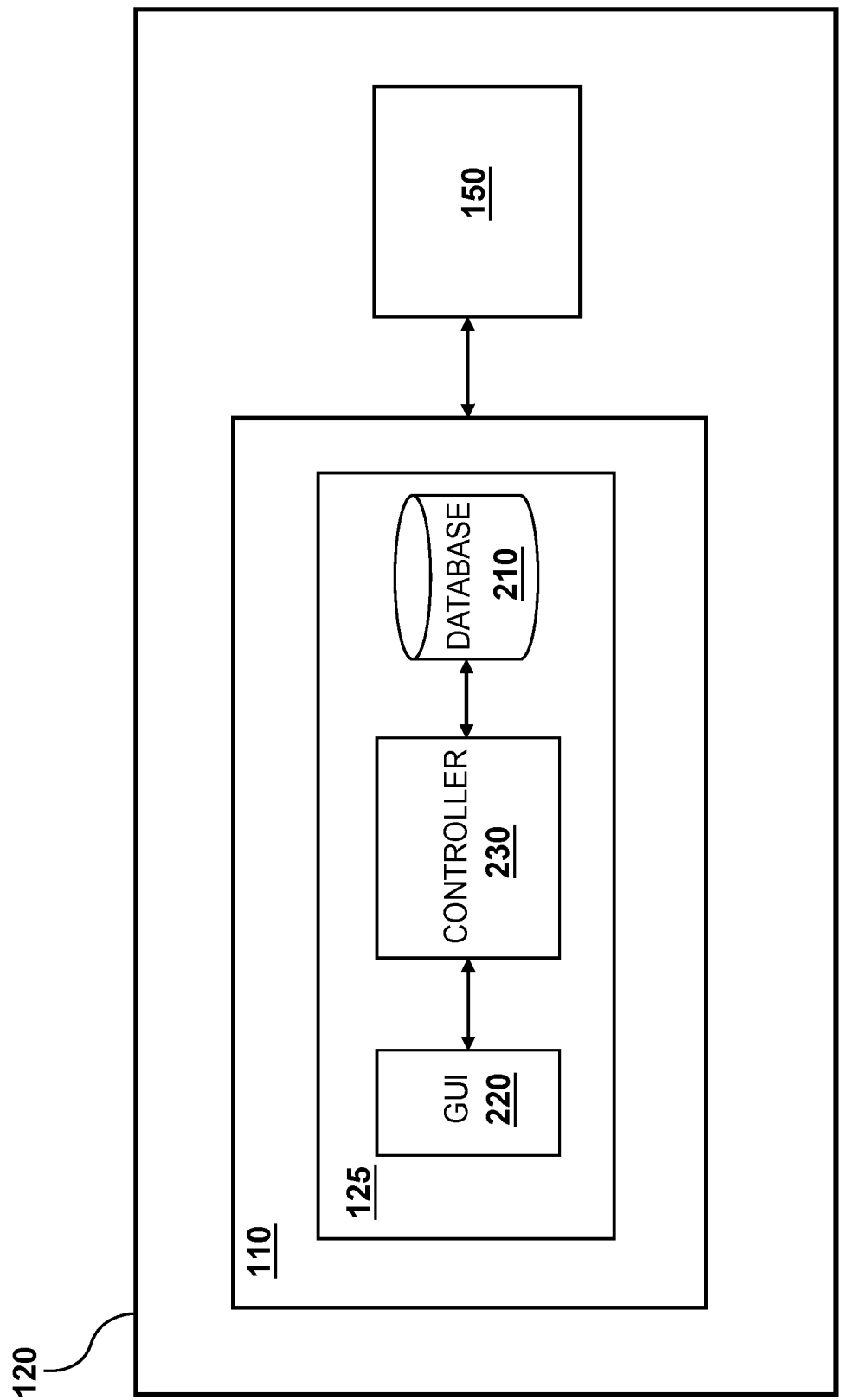
FIG. 2 is a block diagram of a server component of the system of FIG. 1.

FIG. 2 is a simplified schematic depiction of the server 120 in isolation from the remainder of the system 100 of FIG. 1. It will be appreciated that some components of server 120 are omitted from FIG. 2 for brevity.

As illustrated, the server 120 comprises at least one processor 150 communicatively coupled with memory 160 storing the application 125. In the present embodiment, the application 125 comprises three modules: a database 210, a graphical user interface (GUI) 220, and a controller 230. These three modules 210, 220, and 230 may for example be implemented using a Model-View-Controller software architecture. In this architecture, the Model component may comprise back-end application data, the View component may comprise a user interface that is generated based in part on the application data, and the Controller component may comprise the "business logic" of the application that interprets user inputs, collects appropriate data from the back-end application data, and assembles it appropriately for the View component to present to a user. It will be appreciated that the database 210, GUI 220, and controller 230 correspond to the Model, View, and Controller components, respectively, of such an architecture. The controller 230 may be communicatively coupled to each of the database 210 and the GUI 220, as depicted, e.g., via Application Programming Interface (API) calls.

Figure 3:
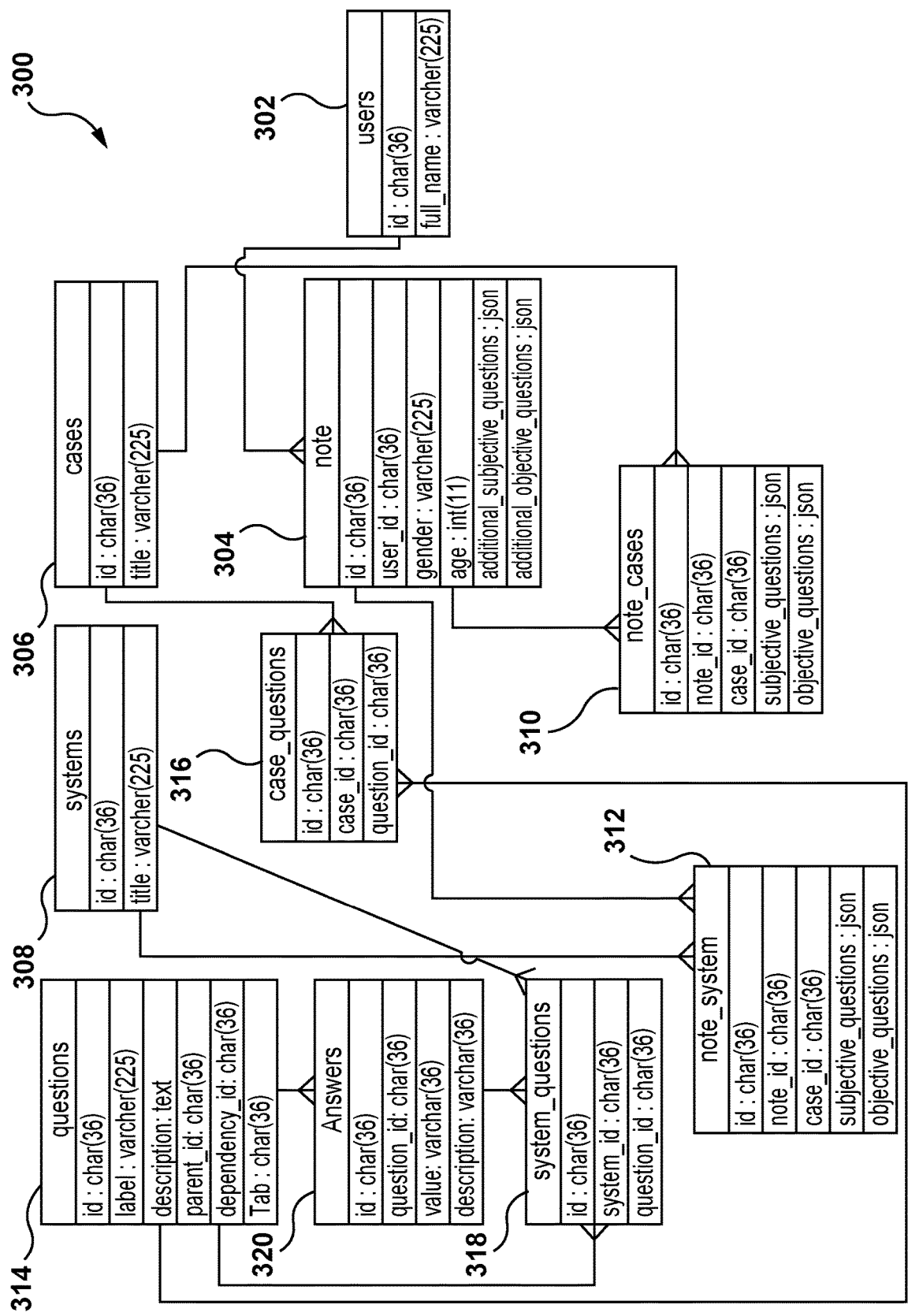
FIG. 3 is an entity relationship diagram depicting relationships between various types of records of a database of the system of FIG. 1.

In some embodiments, the database 210 of FIG. 2 may comprise a relational database whose architecture conforms to the database diagram 300 (a form of entity relationship diagram) of FIG. 3. Referring to FIG. 3, each block of the diagram represents a distinct type of database record (entity).

The database diagram 300 of FIG. 3 defines ten distinct database record types: users 302, note 304, cases 306, systems 308, note_cases 310, note_system 312, questions 314, case_questions 316, system_questions 318, and answers 320. In FIG. 3, the name of each record is indicated in the header at the top of the respective block, and attributes of the record are depicted as respective rows within the block. Moreover, a line from a first box to a second box ending with a "crow's foot" at the second box indicates a "one-to-many" relationship between the first and second database records, respectively. Each of the ten record types has multiple attributes, as described in Table 1 below. It will be appreciated that some attributes and/or database record types of system 100 may be omitted from FIG. 3 for brevity.

TABLE 1

Database Record Types

| Record Name | Description | Attributes |
|---|---|---|
| 1. users | A user of system 100 (e.g., doctor 102) | id: unique user ID<br>full_name: name of user |
| 2. note | A record of a particular medical appointment with a patient, i.e., a patient encounter | id: unique note ID<br>user_id: unique ID of patient<br>gender: gender of patient<br>age: age of patient<br>additional_subjective_questions: array or collection of unique question IDs of individually chosen questions regarding subjective conditions of the patient to be posed to the patient during the medical appointment<br>additional_objective_questions: array or collection of unique question IDs of individually chosen prompts prompting objective observations of the patient to be made during the medical appointment |
| 3. cases | A type of medical case or complaint (e.g., headache, dizziness, etc.) | id: unique case ID<br>title: title of medical case |
| 4. systems | A distinct body system (e.g., pulmonary, respiratory, etc.) | id: unique system ID<br>title: name of system |
| 5. note_cases | For a particular medical case: an associated set of questions to be posed to a patient presenting with the medical case, the questions regarding | id: unique ID of the note_cases record<br>note_id: unique ID of the associated note (specific to a patient encounter)<br>case_id: unique ID of a type of medical case (e.g., headache, dizziness, etc.)<br>subjective_questions: array or collection of question IDs of questions to be posed to the patient presenting with the medical case |

TABLE 1-continued

Database Record Types

| Record Name | Description | Attributes |
| --- | --- | --- |
| | subjective patient conditions and; an associated set of prompts for making objective observations of the patient presenting with the medical case | during the medical appointment objective_questions: array of question IDs of prompts for making objective observations of the patient presenting with the medical case during the medical appointment |
| 6. note_system | for a particular body system: an associated set of questions to be posed to a patient to assess the relevant body system, the questions regarding subjective patient conditions and; an associated set of prompts for making objective observations of the patient to assess the relevant body system of the patient | id: unique ID of the note_cases record note_id: unique ID of the associated note (specific to a patient encounter) system_id: unique ID of a body system (e.g., pulmonary, respiratory, etc.) subjective_questions: array of question IDs of questions to be posed to the patient during the medical appointment regarding the relevant body system objective_questions: array or collection of question IDs of prompts for making objective observations of the patient during the medical appointment regarding the relevant body system |
| 7. questions | A question to pose to the patient OR a prompt for making an objective observation of the patient (in this document, a "prompt" may be considered as a form of question) | id: unique question ID or prompt ID label: label of the question or prompt (i.e., the question text or prompt text) description: text of the question or prompt (i.e., further explanatory information/directions for the user regarding the question or prompt, e.g., as may be revealed upon hovering a mouse pointer over the question/prompt) parent_id: for sub-questions of a hierarchy, a unique ID of the parent question dependency_id: for questions of a hierarchy, a unique ID of a subordinate question Tab: the GUI region in which the question/prompt is to be populated - either "subjective" (for questions regarding a subjective condition of the patient) or "objective" (for prompts to make an objective observation of the patient) |
| 8. case_questions | A question to pose to the patient OR a prompt prompting an objective observation of the patient who presents with a particular medical case | id: unique case question/prompt ID case_id: unique ID of relevant medical case question_id: unique ID of question/prompt to be posed/prompted during examination of patient with the indicated medical case |
| 9. system_questions | A question to pose to the patient OR a prompt prompting an objective observation of the patient during assessment of a particular body system | id: unique system question ID system_id: unique ID of relevant body system question_id: unique ID of question/prompt to be posed/prompted when assessing the indicated body system |
| 10. Answers | A predetermined possible response to a question and/or prompt | id: unique answer ID question_id: ID of associated question/prompt label: label of the answer (i.e., the question text or prompt text) description: explanatory text, e.g., explaining what the "answer" means |

The types of medical cases that may be represented by a "cases" record 306 include, but are not limited to, medical cases as may be seen in family medicine or a general medical practice.

The types of body systems that may be represented by a "system" record 306 include, but are not limited to, body systems as may be commonly treated in family medicine or a general medical practice.

Example operation of the system 100 shall be described with reference to FIG. 4-17. For this description, it is presumed that the user of the system 100 is doctor 102 (FIG. 1), who has just commenced a medical appointment with patient 104, e.g., in a clinical setting such as a doctor's office. The doctor 102 may hold the local computing device 110, e.g., a tablet device, in his or her hand as the medical appointment transpires.

Initially, the doctor 102 may use the browser 115 of tablet 110 to invoke the web application 125, which may be hosted at a predetermined URL of the world wide web. Upon invocation of application 125, the GUI module 220 may initially display a preliminary user interface screen as depicted in FIG. 4.

Figure 4:
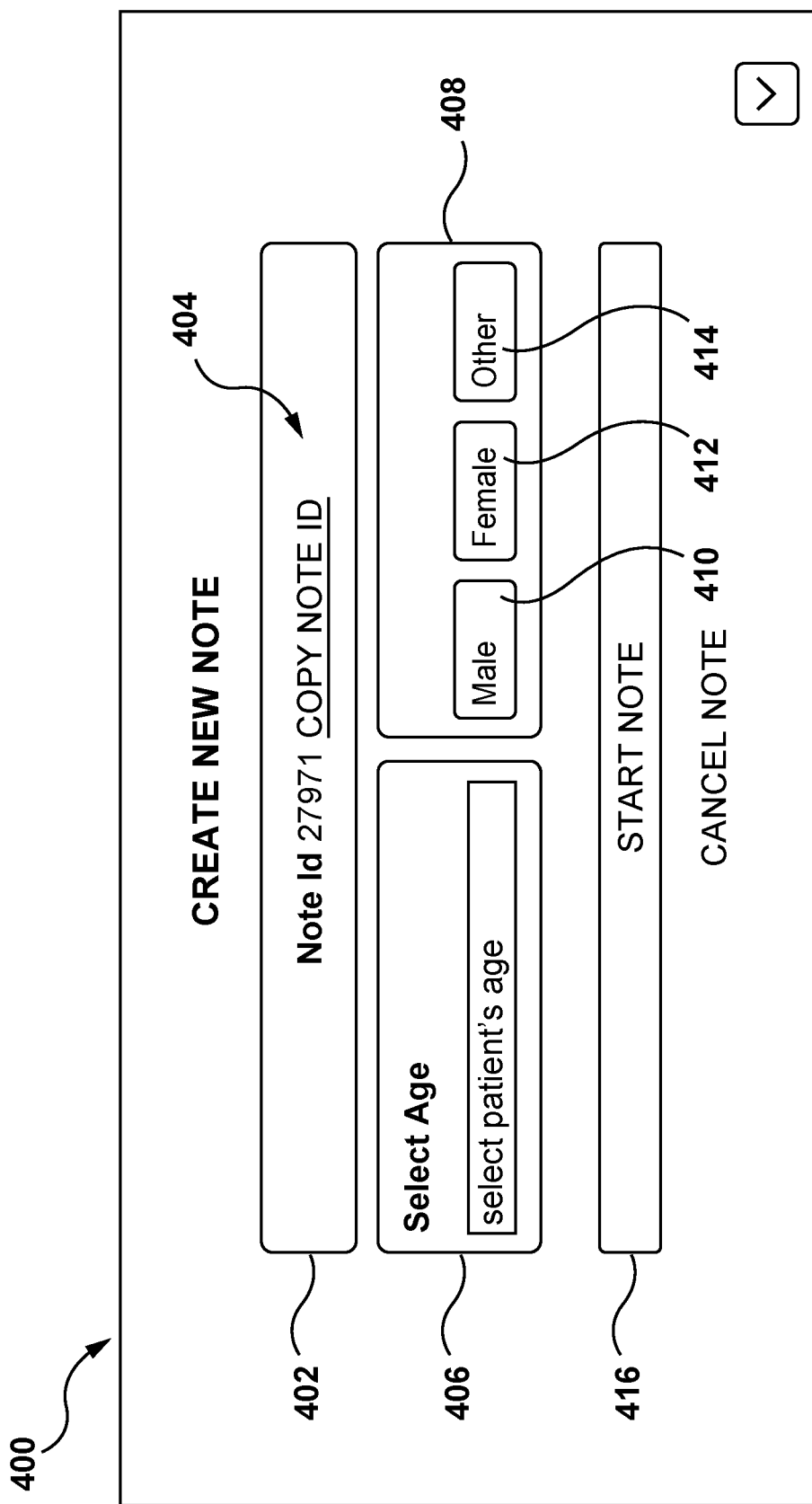
FIG. 4 is an example graphical user interface (GUI) screen that may be generated by the system of FIG. 1.

Referring to FIG. 4, the example preliminary user interface screen 400 includes the fixed language "Create New Note," inviting the user to generate a new record of a medical appointment. In the depicted embodiment, a text field 402 contains an automatically generated unique note ID ("27971") and a "Copy Note ID" hyperlink 404 that may be used to automatically copy the note ID to a clipboard of the browser 115. Such automatic copying of the note ID may for example facilitate cutting and pasting of the Note ID to another software application, e.g., an electronic document or legacy clinical software application (neither being expressly depicted).

A first data entry field 406 of screen 400 may permit an age of the patient to be specified. A second data entry field 408 may permit specification of a gender of the patient via selection of one of three buttons 410, 412, and 414. The specified gender may influence the content of the GUIs that are dynamically populated by application 125. In this embodiment, the application 125 refrains from collecting information specifically identifying the patient, such as name, address, or social security number, e.g., to comply with privacy regulations that may be jurisdiction-specific.

The example GUI screen 400 also contains a button 416 for triggering the creation of a new note, which may serve as a record of the medical appointment with a patient 104. As will be appreciated, the record may avoid the need for a manual record generation, e.g., typing on a keyboard, which may be tedious, slow, and error-prone. In the present embodiment, selection of button 416 causes a "note" record 304 to be instantiated in database 310 (FIG. 3) with the "id" attribute set to the note ID shown in text field 402 of FIG. 4 and the "gender" and "age" attributes set to whatever gender and age information was specified via data entry fields 406 and 408 of FIG. 4, respectively.

Figure 5:
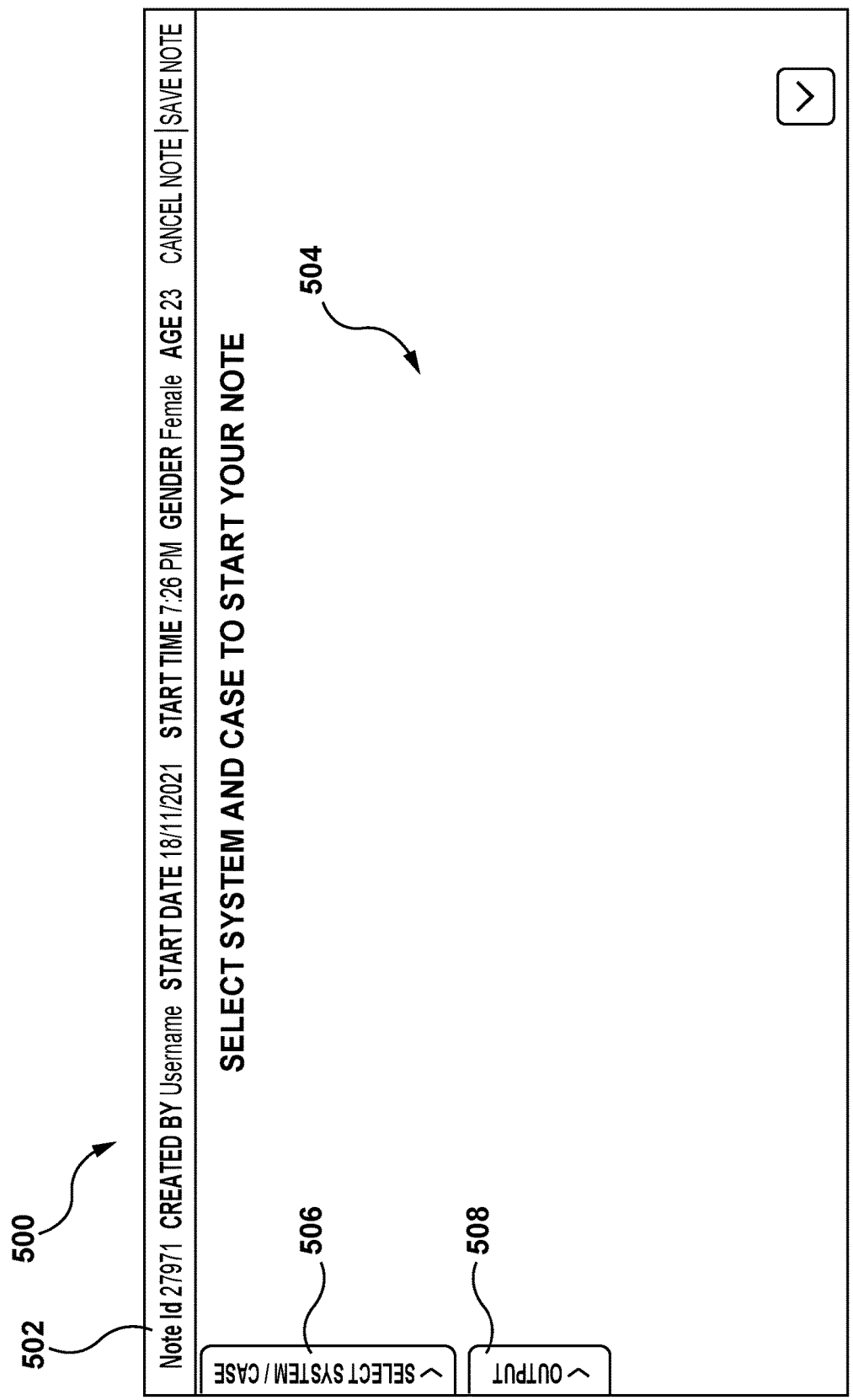
FIG. 5 is a further example GUI screen that may be generated by the system of FIG. 1.

In the present embodiment, selection of button 416 of FIG. 4 also causes the GUI screen 500 of FIG. 5 to be displayed. Referring to FIG. 5, the example GUI screen 500 includes a header 502 with various note-specific information, such as note ID, username of the user, a date and time at which the note was created, and patient gender and age information. The GUI screen 500 also has a body 504 where a patient-specific GUI can be dynamically created and then immediately used. In FIG. 5, the body 504 of GUI screen 500 is initially blank (unpopulated or empty), which may be its initial default state upon note creation. As will be appreciated, the body 504 of GUI screen 500 will define or contain two independently user-selectable GUI regions— each a tab in the present embodiment—that will be dynamically populated with subjective questions and prompts, respectively.

In the present embodiment, two vertically oriented, expandable tabs 506 and 508 are displayed at the left-hand side of GUI screen 500. An expandable tab (also known as an "accordion") is a form of user-selectable GUI section or pane that can be selectively expanded (brought into focus via expansion of the tab) and collapsed (hidden). The first expandable tab 506, labeled "Select System/Case," facilitates user specification of one or more medical cases with which the patient has presented during the current medical appointment and/or one or more body systems to be assessed during the current medical appointment, as will be described below. The second expandable tab 508, labeled "Output," may provide a current snapshot of textual output that may be automatically generated based on any responses to subjective questions and/or any objective observations of the patient 104 completed to date during the medical appointment.

Figure 6:
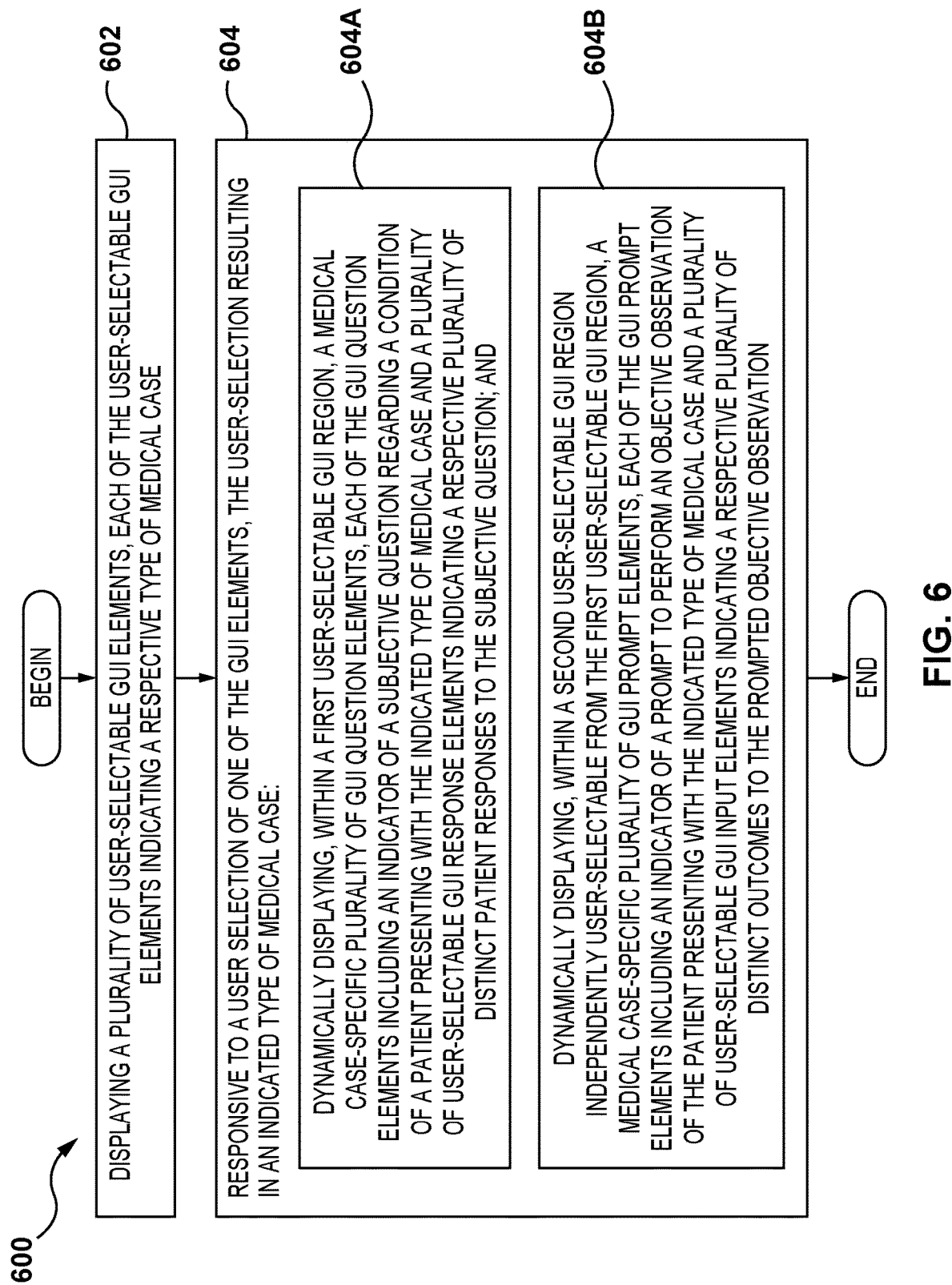
FIG. 6 is a flowchart of operation of the system of FIG. 1.

FIG. 6 is a flowchart of operation 600 of system 100 for facilitating medical appointment record creation with a minimum of user input actions. In operation 602 (FIG. 6), a plurality of buttons 700—each a form of user-selectable GUI element—is displayed on the display 114 of computing device 110. In the present embodiment, the buttons 700 are presented on the expandable tab 506 of GUI screen 500, as shown in FIG. 7.

Figure 7:
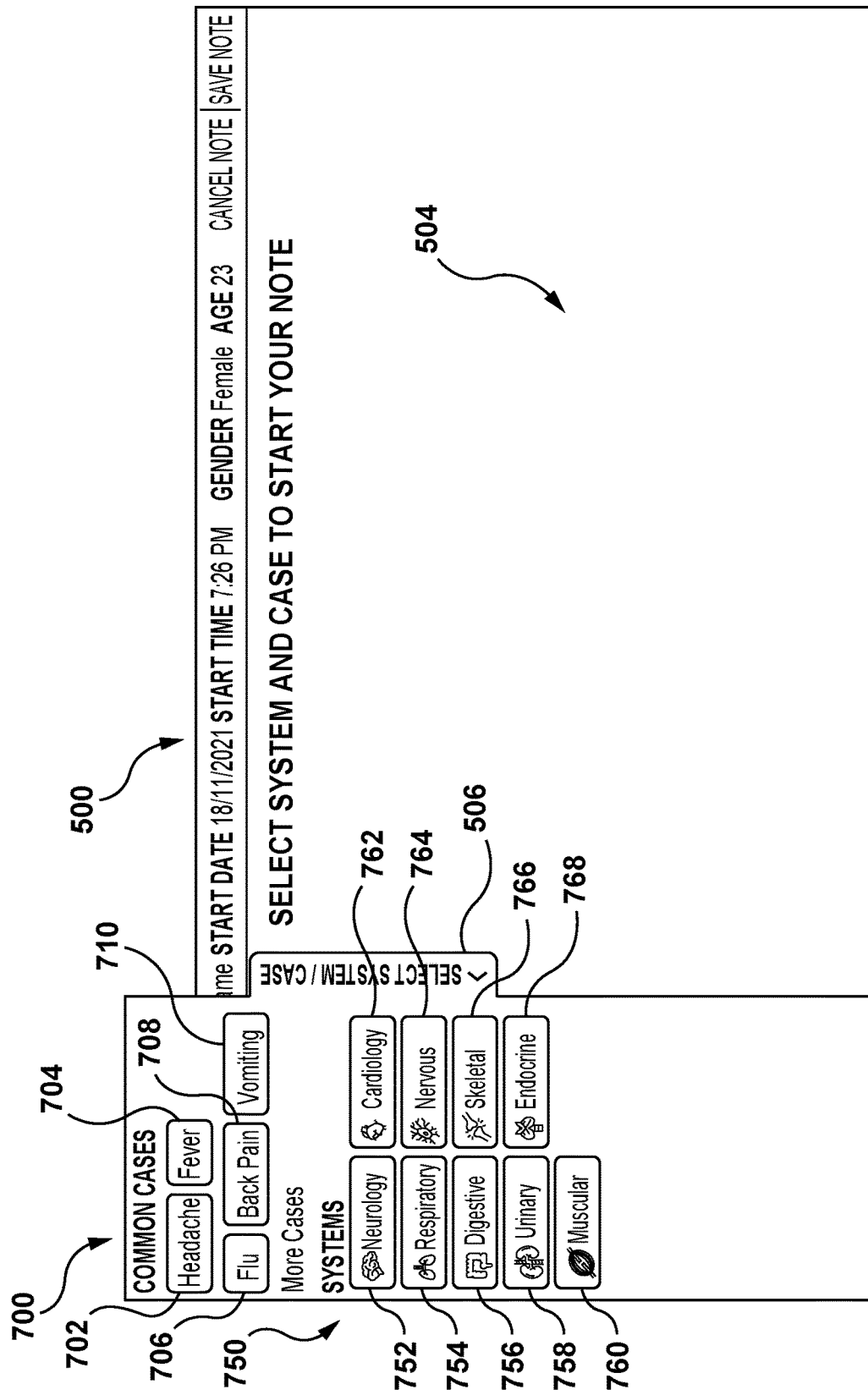
FIG. 7 is a further example GUI screen that may be generated by the system of FIG. 1 during the operation of FIG. 6.

FIG. 7 depicts tab 506 of GUI screen 500 in an expanded state after operation 602 has been performed. In the present embodiment, operation 602 has resulted in the display of five buttons 700 in tab 506, each button indicating a respective type of medical case. More specifically, the five buttons 702, 704, 706, 708, and 710 indicate the medical cases of headache, fever, flu, back pain, and vomiting, respectively. The medical cases indicated by the GUI elements 700 of alternative embodiments may differ. In some embodiments, the set 700 of GUI elements may be user-configurable in number and in respect of the indicated medical cases, e.g., via an admin dashboard (not expressly depicted). This may facilitate user customization of the system 100 for different types of medical practices.

For illustration, it is presumed that the main complaint of the patient 104 is a headache. The doctor 102 may accordingly select the "Headache" button 702 of tab 506 to indicate that the medical case at issue for the patient 104 is that of a headache. This user selection may cause the button 702 to change in appearance (e.g., to become highlighted—not shown in FIG. 7) to denote the user selection. The user selection also triggers dynamic population of the GUI screen 500 with case-specific content pursuant to operation 604 of FIG. 6. In particular, two sub-operations 604A and 604B are performed.

In sub-operation 604A, a medical case-specific set of multiple GUI question elements is dynamically displayed within a first user-selectable GUI region. In other words, the first user-selectable GUI region is automatically populated with a predetermined set of multiple GUI question elements specific to the "Headache" medical case. Each GUI question element includes an indicator of a subjective question regarding the condition of a patient presenting with the indicated type of medical case (a headache in this example) and multiple user selectable GUI response elements indicating a respective plurality of distinct patient responses to the subjective question. For clarity, a set of question elements may be considered specific to a type of medical case even if one or more of the question elements of the set is also relevant to or associated with one or more other types of medical cases.

Figure 9:
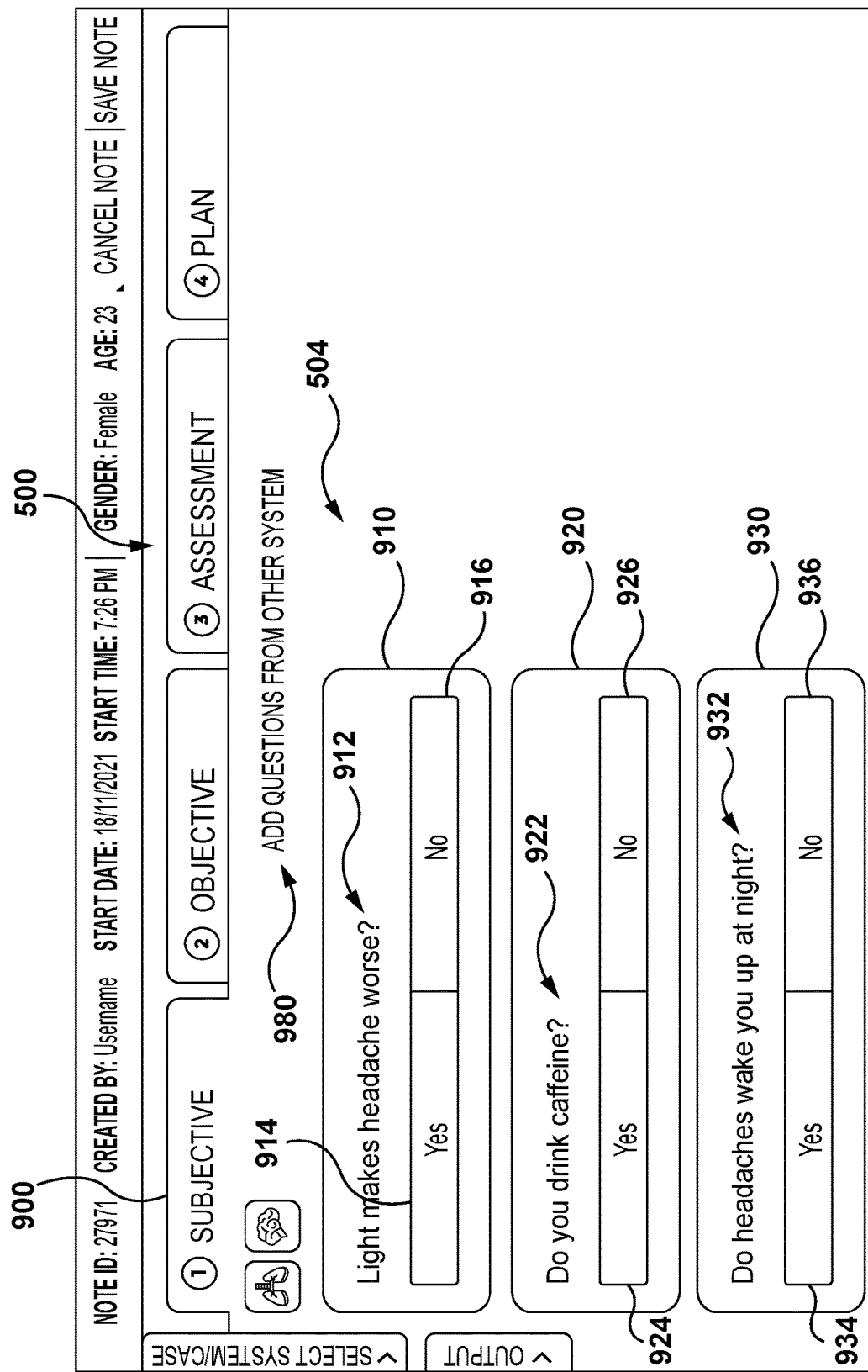
FIG. 9 is an example GUI screen that may be generated by the system of FIG. 1 on completion of the operation of FIG. 6.

In the present embodiment, the first user-selectable GUI region is a tab—referred to as the "subjective tab 900," as shown in FIG. 9, described below—for displaying question elements regarding a subjective condition of the patient 104.

In the present example, sub-operation 604A causes three question elements to be added to the subjective tab 900, as depicted in FIG. 9 (described below). It will be appreciated that the number of question elements (i.e., three) is intentionally small in this example for brevity and comprehensibility and that the number of question elements in alternative embodiments may be higher than three.

Each user-selectable GUI response element may be operable to automatically record the indicated response, e.g., in a data structure, record, or file documenting the medical appointment, upon its selection. In some embodiments, selection of a GUI response element may cause a new record "note_question" to be instantiated in a relational database. This record represents a subjective question that has been answered, e.g., as distinct from any subjective questions that are unanswered. Whatever answer(s) to the question have been selected may be captured in associated new instances of a record "note_question_answers." In the present embodiment, the user-selectable GUI response elements are buttons with predetermined answers such as "yes" or "no," as will be described below in connection with FIG. 9, which shows the GUI after its population.

In sub-operation 604B (FIG. 6), a medical case-specific set of multiple GUI prompt elements is dynamically displayed within a second user-selectable GUI region that is independently selectable from the first GUI region. In other words, the second user-selectable GUI region is automatically populated with a predetermined set of multiple GUI prompt elements specific to the "Headache" medical case. Each GUI prompt element includes an indicator of a prompt to perform an objective medical observation of the patient presenting with the indicated type of medical case (a headache in this example) and multiple user-selectable GUI input elements indicating a respective plurality of distinct outcomes of the prompted observation. In this example, objective observations of a patient may include, e.g., taking a pulse, measuring heart rate, and the like, possibly using appropriate medical equipment (e.g., a stethoscope, a blood-pressure measurement device, etc.). For clarity, a set of prompt elements may be considered specific to the type of medical case even if one or more prompt elements of the set is also relevant to another type of medical case.

Figure 10:
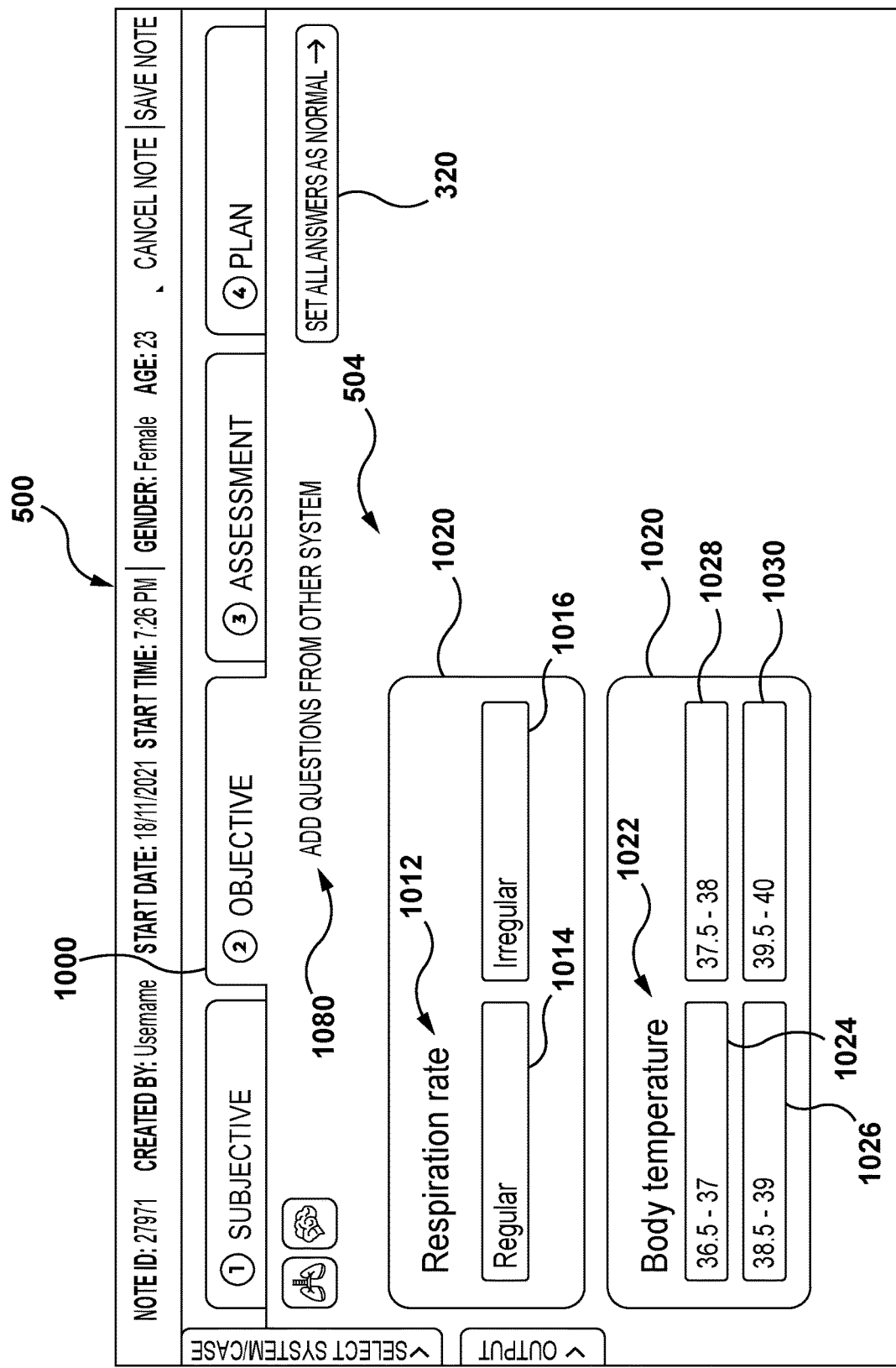
FIG. 10 is another example GUI screen that may be generated by the system of FIG. 1 on completion of the operation of FIG. 12.

In the present embodiment, the second GUI region is the objective tab 1000 shown in FIG. 10. In this example, two prompt elements will be added to the objective tab 1000, as depicted in FIG. 10 (described below).

In the present embodiment, the user-selectable GUI input elements are buttons indicating predetermined answers such as "yes" or "no," as will be described below in connection with FIG. 10. Each GUI input element may be operable to automatically record the indicated outcome, e.g., in a data structure, record, or file documenting the medical appointment, upon its selection. In some embodiments, selection of a GUI input element may cause a new record "note_question" to be instantiated in a relational database. This record represents a prompted objective observation for which an outcome has been recorded, e.g., as distinct from an objective observation for which no outcome has been recorded. Whatever outcome(s) to the prompted objective observation have been selected may be captured in associated new instances of a record "note_question_answers."

It will be appreciated that sub-operations 604A and 604B of operation 604 (FIG. 6) do not necessarily occur in sequential order.

Figure 8:
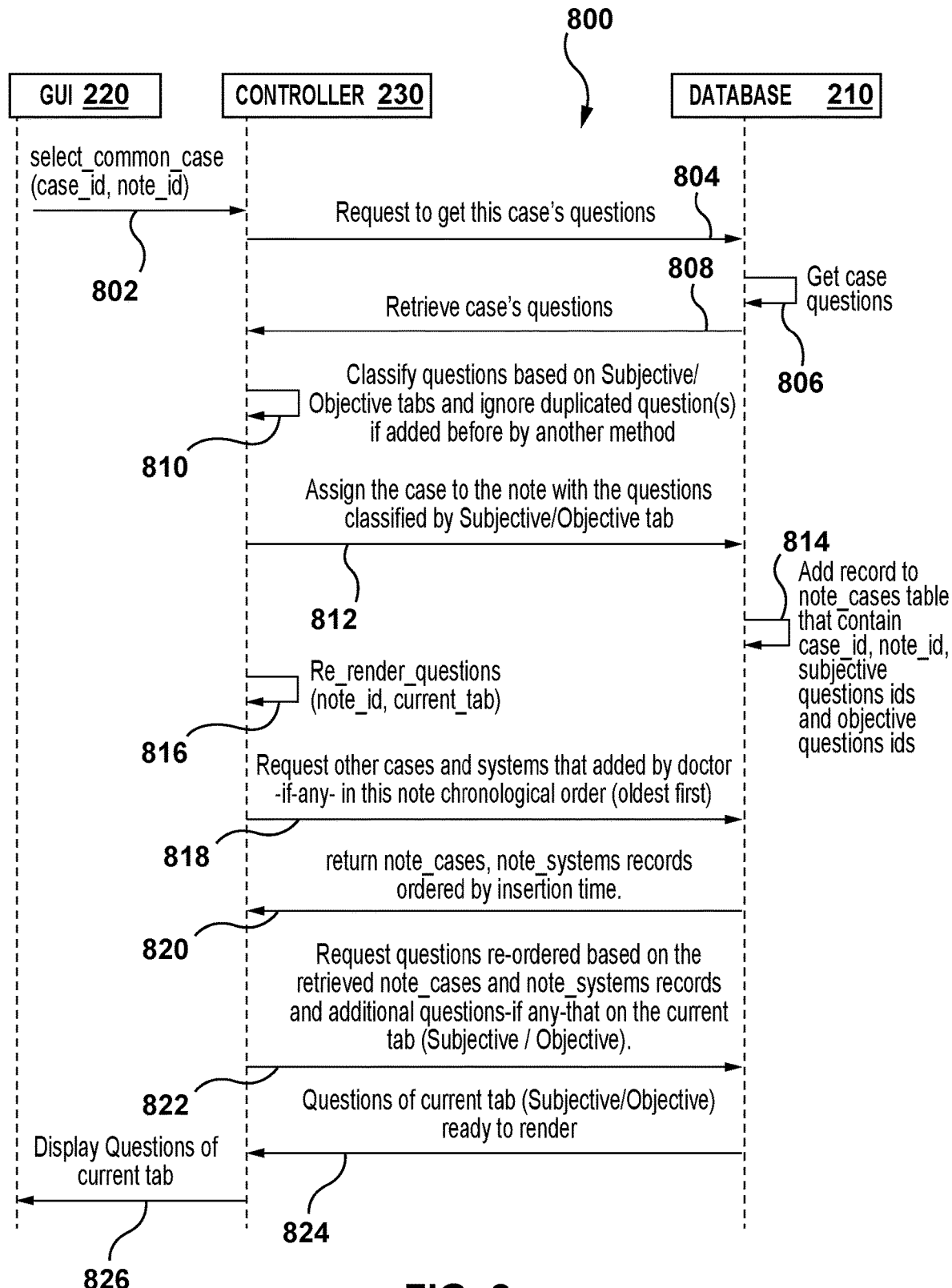
FIG. 8 is a sequence diagram depicting one implementation of the operation of FIG. 6.

In some embodiments, operation 604 of FIG. 6 may be implemented by way of interactions between the database 210, GUI 220, and controller 230 modules of application 125 (FIG. 2) as depicted in the sequence diagram 800 of FIG. 8.

More specifically, operation 802 of FIG. 8 may be triggered by user selection of the "headache" button 702 of FIG. 7. In operation 802, the GUI module 220 may invoke a method "select_common_case" of the controller 230, passing two parameters. The first parameter is the unique case ID of the "headache" case. The second parameter is the unique note ID of the current note.

At the controller module 230, the invoked select_common_case method may trigger a database query requesting all of the questions and/or prompts associated with the medical case "headache" (operation 804, FIG. 8). Although not expressly shown, the query may pass as a parameter the unique case_id of the "headache" case.

At the database module 210, the query may be completed as shown in operation 806. In the present embodiment, operation 806 may retrieve all case_question records 316 whose case_id matches the "headache" unique case ID. In this simplified example, five such case_question records 316 are returned. Three of the case_questions records 316 represent three respective subjective questions to be posed to a patient presenting with a headache. The remaining two records 316 represent two respective prompts, each for making an objective observation of the patient presenting with the headache. The five records may be returned to the controller 230 in operation 808 (FIG. 8). It will be appreciated that the number of questions and prompts described above is merely illustrative and that the number of questions/prompts for a thorough medical assessment of a patient exhibiting headache symptoms may actually be greater than five.

In operation 810 (FIG. 8), the five returned case_questions records may be classified into two groups: subjective questions for the patient that are associated with the "Headache" case and prompts for making objective observations of the patient that are associated with the "Headache" case. In the present embodiment, the classification is based upon whether the "Tab" attribute of the associated questions record 314 is "subjective" or "objective," respectively. In some embodiments, the single query of operations 804 and 806 may instead comprise with two separate queries, each query being specific to a respective one of the "subjective" and "objective" values for the "Tab" attribute of the "questions" record 314.

In the present embodiment, operation 810 may include processing for avoiding redundancy in the questions/prompts of the current note. This processing contemplates the possibility that the question/prompts of different medical cases, such as "headache" and, say, "vomiting," may at least partially overlap, in the sense that each of the two medical cases may warrant asking the patient the same question (e.g., "Are you experiencing weakness in any part of the body?") or prompting the user to make the same objective observation (e.g., "Take patient blood pressure"). The redundancy-avoidance processing also contemplates the possibility that the questions/prompts associated with a medical case may span multiple body systems, whose associated questions/prompts may have independently been added to the current note in some other fashion (e.g., via the functionality described in FIGS. 11 and 12, described below).

In the present embodiment, redundancy-avoidance processing may for example entail removing any of the case_questions records 316 returned in operation 808 (FIG. 8) whose question_id attribute identifies a questions record 314 that has already been associated with the note record 304 in some fashion, e.g., via a case_questions record 316, via a system_questions record 318, or by being enumerated in the array of either the additional_subjective_questions attribute or the additional_objective_questions attribute of the note record 304.

In the present example, in which the "headache" case is the first case to be selected for the current note, no note_cases records have been previously associated with the current note record 302. All of the five questions/prompts in the present example are accordingly new to the note, i.e., no redundant questions/prompts are found to exist in operation 810.

In operation 812 (FIG. 8), the non-redundant questions/prompts classified in operation 810 are added to the current note. This may for example be performed by passing to the database module 210 a first parameter comprising all the unique IDs of the three case_questions records 316 representing subjective questions and a second parameter comprising the unique IDs of the two case_questions records 316 representing prompts.

In operation 814 (FIG. 8), a new note_cases record 310 is created and added to the database 210. The note_id attribute of the new record 310 is set to the current note ID. The case_id attribute of the new record is set to the unique case_id associated with the "headache" medical case. The subjective_questions attribute of the new record (which may be a collection or array, e.g., in JavaScript Object Notation (JSON)) is populated with the three unique IDs of the subjective questions identified in operation 810. The objective_questions attribute of the new record (which may be a collection or array, e.g., in JSON) is populated with the two unique IDs of the objective questions, i.e., prompts, identified in operation 810.

In operation 816, the controller 230 invokes a method Re_render_questions, passing two parameters: the unique note_ID of the current note, and a current_tab variable. The current_tab variable uniquely identifies whichever one of subjective tab 900 and objective tab 1000 is currently a focus of GUI screen 500. A tab may for example be considered to be a "focus" of the GUI screen 500 when the tab has been selected either by the user or automatically in software, e.g., so that visible GUI elements (e.g., buttons) of the tab are user-selectable. Operation 816 may be considered as preparing the current tab 900 or 1000 for display to the user with newly populated questions/prompts. In some embodiments, operation 816 may entail four sub-operations 818, 820, 822, and 824, as shown in FIG. 8.

In sub-operation 818, the database 210 may be queried for all note_cases records 310 and note_system records 312 (the latter being described in more detail below in connection with the description of FIG. 11) whose note_id attribute matches the unique ID of the current note, in chronological order. The reason for the chronological ordering is to ensure that, as questions/prompts are progressively added to a note, e.g., through progressive user selection of medical cases afflicting the patient 104 and/or body systems of the patient to be examined, the questions/prompts are added and maintained in a consistent order within the GUI.

In sub-operation 820 (FIG. 8), all of the note_cases records 310 and note_systems records 312 whose note_id attribute matches the unique ID of the current note are returned in chronological order by insertion time. In this example, sub-operation 820 returns only the most recently added note_cases record 310 associated with the "headache" medical case, because in this scenario no other medical cases or body systems have been previously specified for this note via the buttons 700 or 750 of expandable tab 506 (FIG. 7).

The result of operation 820 may be a set of unique question IDs (for subjective tab 900) and prompt IDs (for objective tab 1000) ordered as they should appear in their respective tabs.

In sub-operation 822 (FIG. 8), the set of question IDs resulting from operation 820 may be sent to the database 210 for retrieval of both the label attribute of the corresponding questions record 314 and the predetermined responses (answer records 320) associated with each question/prompt for the current tab.

In sub-operation 824 (FIG. 8), the labels and predetermined responses associated with each question/prompt requested in sub-operation 822 are returned from the database module 210.

In operation 826 (FIG. 8), the GUI module 220 displays the populated body 504 of GUI screen 500 with the first user-selectable GUI region (subjective tab 900) or the second user-selectable GUI region (objective tab 1000) being visible, depending upon which of the two tabs 900 and 1000 is in focus (i.e., is the "current_tab"). Presuming that the subjective tab 900 is in focus, the result of operation 826 may be as depicted in FIG. 9.

FIG. 9 depicts the GUI screen 500 upon completion of operation 600 of FIG. 6. As illustrated, the body 504 of GUI screen 500 is now populated with three question elements 910, 920, and 930 pertaining to the medical case of "Headache." In the present embodiment, each question element is graphically represented as a rounded rectangular panel defining a form of boundary. Each panel contains an indicator of the question, e.g., textual indicators 912, 922, and 932 of question elements 910, 920, and 930 respectively. Also displayed as part of each question element (here, within the boundary) is a plurality of buttons, e.g., buttons 914 and 916 of question element 910; buttons 924 and 926 of question element 920; and buttons 934 and 936 of question element 930. Each of the buttons is a form of user-selectable GUI response element representing a distinct patient response to the associated question. Other forms of GUI response elements, such as radio buttons, pulldown menus, or interactive calendars, could be used in alternative embodiments.

Rendering of question element 910 may for example entail rendering with the textual value of the "label" attribute of the questions record 314 (FIG. 3) displayed as a textual indicator 912 within the panel boundary. For each instance of the "Answer" record 320 (FIG. 3) associated with the relevant question record 314, a respective button 914 or 916 may also be rendered within the panel boundary. The label of each button 914 and 916 may be set to the value of the "label" attribute of the respective instance of the "Answer" record 320 (here, "Yes" and "No," respectively). The other question elements 920 and 930 may be similarly rendered.

To the extent that the objective tab 1000 (the second GUI region, only partially visible in FIG. 9) is the current tab, the result of operation 606 of FIG. 6 may be to display the GUI screen 500 with the populated objective tab 1000 visible as shown in FIG. 10.

FIG. 10 depicts the GUI screen 500 with the body 504 having been populated with two prompt elements 1010 and 1020. In the present embodiment, each prompt element is graphically represented as a rounded rectangular panel containing an indicator of the prompt (e.g., textual indicators 1012 and 1022 within prompt elements 1010 and 1020 respectively). Also displayed as part of each prompt element (here, within the panel boundary) is a plurality of buttons (e.g., buttons 1014 and 1016 of prompt element 1010, and buttons 1024, 1026, 1028, and 1029 of prompt element 1020). It will be appreciated that each of the buttons is a form of user-selectable GUI input element that indicates a respective outcome of the objective medical observation of the patient prompted by the associated prompt. For example, buttons 1014 and 1016 indicate respective outcomes of "Regular" and "Irregular" of an objective observation of a respiration rate made in response to prompt indicated at 1012. Other forms of user-selectable GUI input elements, such as radio buttons, pulldown menus, or interative calendars, could be used in alternative embodiments.

A possible rationale for populating question elements regarding respective subjective conditions of the patient in a first user-selectable GUI region (e.g., subjective tab 900 of FIG. 9) and populating prompt elements for making objective observations of the patient in a second user-selectable GUI region (e.g., objective tab 1000 of FIG. 10) may be to promote run-time efficiency of the system 100 in relation to the manner in which a medical appointment may be conducted. For example, a doctor 102 may prefer to have a patient 104 initially answer questions regarding subjective conditions of the patient all at once, e.g., at the beginning of a medical appointment (e.g., "How are you sleeping?" and "Does noise make your headache worse?"). The responses of the patient 104 may be immediately recorded by user interaction exclusively with the GUI response elements in the subjective tab 900 (e.g., tapping to select response buttons on a touchscreen). The doctor 102 may similarly prefer to perform all objective observations of the patient 104 at once, e.g., during a subsequent examination portion of a medical appointment (e.g., taking blood pressure, heart rate, etc.). These objective observations may similarly be easily recorded by user selection of the objective tab 1000 and user interaction exclusively with the GUI input elements (e.g., again by tapping to select response buttons on a touchscreen) of objective tab 1000. Such usage of the system 100 may help to minimize the number of user input actions required to generate a record of the medical appointment.

To the extent that a patient 104 exhibits multiple medical cases during a single appointment (e.g., a headache and vomiting), multiple ones of the "Cases" buttons 700 in tab 506 (FIG. 7) may be selected. Sub-operations 604A and 604B of FIG. 6 may be performed for each one of the medical cases whose button was selected. This may entail executing operations 802-826 of sequence diagram 800 once for each selected medical case.

During the medical appointment, the doctor 102 may deem it to be prudent or necessary to more comprehensively assess one or more particular body systems of the patient 104 (e.g., pulmonary, neurological, etc.). In that circumstance, the doctor 102 may use the system 100 to easily populate the GUI with a set of subjective patient questions and prompts for objective observations for the body system(s) in question. Operation 1100 for achieving this result is shown in FIG. 11.

In the description of operation 1100 that follows, it is presumed that the subjective tab 900 and objective tab 1000 have already been populated with question elements and prompt elements, respectively, associated with a previous chosen medical case, as shown in FIGS. 9 and 10 respectively. It will be appreciated that operation 1100 could alternatively be performed with no previous population of the GUI screen 500 with any questions or prompts.

In operation 1102 (FIG. 11), a plurality 750 of user-selectable GUI elements is displayed on the display 114 of computing device 110. In the present embodiment, the GUI elements 750—which are buttons in this example—are displayed on the same expandable tab 506 as the previously described medical case buttons 700. In this example, the buttons 750 appear below the buttons 700 in tab 506.

Referring again to FIG. 7, which shows tab 506 in an expanded state, it can be seen that the set of system buttons 750 in this example includes nine buttons 752, 754, 756, 758, 760, 762, 764, 766, and 768. Each of these buttons indicates a respective physiological system, namely, Neurology, Respiratory, Digestive, Urinary, Muscular, Cardiology, Nervous, Skeletal, and Endocrine, respectively, in this example. The medical cases indicated by the GUI elements 750 of alternative embodiments may differ. In some embodiments, the set 750 of GUI elements may be user-configurable in number and in respect of the indicated body systems, e.g., via an admin dashboard (not expressly depicted). This may facilitate user customization of the system 100 for different types of medical practices.

For this example, in which the patient 104 has presented with a headache, the doctor 102 may for example deem it to be prudent to conduct a full cardiological assessment of the patient 104. The doctor 102 may accordingly select the "Cardiology" button 762. This user selection may trigger dynamic population (augmentation in this example) of the GUI screen 500 pursuant to operation 1104 of FIG. 11. In particular, for each one of the selected body system buttons 750 that is selected by the user, two sub-operations 1104A and 1104B may be performed.

In sub-operation 1104A (FIG. 11), a body system-specific set of multiple GUI question elements is dynamically displayed within the first user-selectable GUI region. In other words, the first user-selectable GUI region (subjective tab 900) is automatically further populated with a predetermined set of question elements specific to the "Cardiology" body system. Each GUI question element includes an indicator of a subjective question regarding a condition of the patient pertaining to the indicated body system and multiple user-selectable GUI response elements indicating a respective plurality of distinct patient responses to the subjective question. In the present embodiment, the user-selectable GUI response elements are buttons with predetermined answers such as "yes," "no," "regular," or "irregular."

In sub-operation 1104B (FIG. 11), a body system-specific set of multiple GUI prompt elements is dynamically displayed within a second user-selectable GUI region. In other words, the second user-selectable GUI region (objective tab 1000) is automatically populated with a predetermined set of multiple prompt elements specific to the "Cardiology" body system. Each GUI prompt element includes an indicator of a prompt to perform an objective medical observation of a patient pertaining to the indicated body system and multiple user-selectable GUI input elements indicating a respective plurality of distinct outcomes to the prompted objective observation. In the present embodiment, the user-selectable GUI input elements are buttons textually indicating predetermined outcomes, as will be described below in connection with FIG. 15. At this stage, the GUI may be immediately used, e.g., to record the doctors observations of the patient pertaining to the "Cardiology" body system.

It will be appreciated that sub-operations 1104A and 1104B of operation 1104 (FIG. 11) do not necessarily occur in sequential order.

Figure 12:
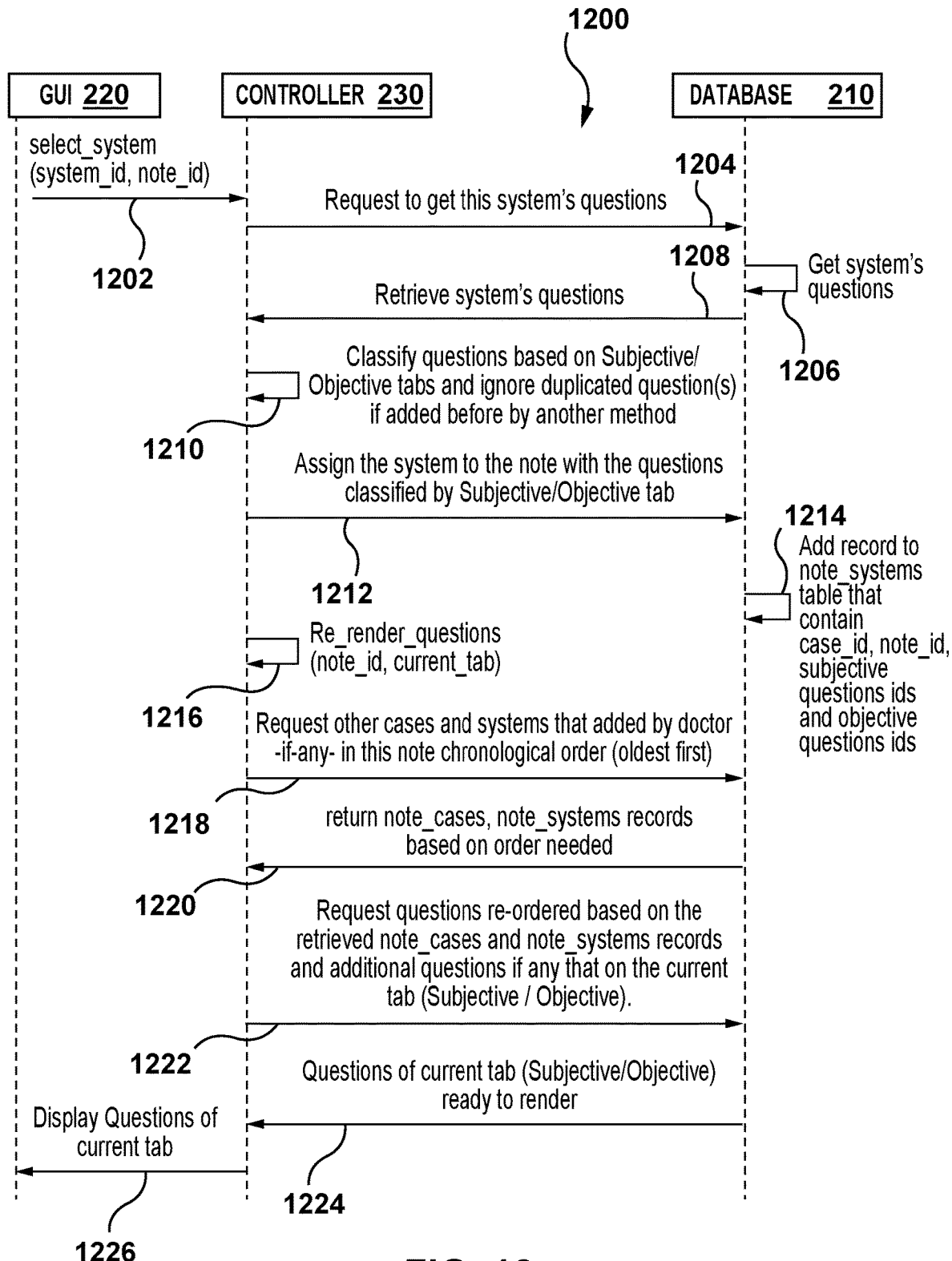
FIG. 12 is a sequence diagram depicting one implementation of the operation of FIG. 11.

In some embodiments, operation 1104 may be implemented by way of interactions between the database 210, GUI 220, and controller 230 modules of application 125 (FIG. 2) as depicted in the sequence diagram 1200 of FIG. 12.

Operation 1202 of FIG. 12 may for example be triggered by user selection of the "Cardiology" button 762 of FIG. 7.

In operation 1202, the GUI module 220 invokes a method "select_system" of the controller module 230, passing two parameters. The first parameter is the unique system ID of the "Cardiology" body system. The second parameter is the unique note ID of the current note.

At the controller module 230, the invoked select_system method may trigger a database query requesting all of the questions and/or prompts associated with the body system "Cardiology" (operation 1204, FIG. 12). Although not expressly shown, the query may pass as a parameter the unique system_id of the "Cardiology" body system.

At the database module 210, the query may be completed as shown in operation 1206. In the present embodiment, operation 1206 may retrieve all system_question records 318 whose system_id matches the "Cardiology" unique system ID. In this simplified example, six such system_questions records 318 are returned. Three of the returned system_question records 318 may have respective associated "questions" records with the Tab attribute of "subjective," representing subjective questions to be posed to a patient during a cardiological assessment. The remaining three returned system_question records 318 may have respective associated "questions" records with the Tab attribute of "objective," each of the records representing a respective prompt for making an objective observation of the patient during the cardiological assessment. The six question and prompt records may be returned to the controller 230 in operation 1208 (FIG. 12).

In operation 1210 (FIG. 12), the six returned case_systems records may be classified into two groups: (1) subjective questions for the patient; and (2) prompts for making objective observations of the patient. Optionally, a similar result may be obtained by replacing the single query of operations 1204 and 1206 with two separate queries, each query being specific to a respective one of the "subjective" and "objective" values for the "Tab" attribute of the "questions" record 314.

In the present embodiment, operation 1210 may include processing for avoiding redundancy in the questions/prompts of the current note. This processing contemplates the possibility that the questions and/or prompts associated with the selected body system may at least partially overlap with the questions and/or prompts with which the GUI has already been populated. Such redundancy avoidance processing may for example entail removing any of the system_questions records 318 returned in operation 1208 (FIG. 12) whose question_id attribute identifies a questions record 314 that has already been associated with the note record 304 in some fashion, e.g., via a case_questions record 316, via a system_questions record 318, or by being enumerated in the array of either the additional_subjective_questions attribute or the additional_objective_questions attribute of the note record 304.

In operation 1212 (FIG. 12), the non-redundant questions/prompts classified in operation 1210 are added to the current note. This may for example be performed by passing to the database module 210 a first parameter comprising all the unique IDs of the three non-redundant new system_questions records 318 representing subjective questions and a second parameter comprising the unique IDs of the three new system_questions records 318 representing prompts.

In operation 1214 (FIG. 12), a new note_systems record 312 is created and added to the database 210. The note_id attribute of the new record 312 is set to the current note ID. The system_id attribute of the new record is set to the unique system_id associated with the "Cardiology" body system. The subjective_questions attribute of the new record (which may be a collection or array, e.g., in JSON format) is populated with the unique IDs of the subjective questions identified in operation 1210. The objective_questions attribute of the new record (which may be a collection or array, e.g., in JSON format) is populated with the unique IDs of the objective questions, i.e., prompts, identified in operation 1210.

In operation 1216 (FIG. 12), the controller 230 invokes a method Re_render_questions, passing two parameters: the unique note_ID of the current note, and a current_tab variable. The current_tab variable uniquely identifies whichever one of subjective tab 900 and objective tab 1000 is currently a focus of GUI screen 500. Operation 1216 may be considered as preparing the current tab 900 or 1000 for display to the user with the newly populated questions/prompts and may entail four sub-operations 1218, 1220, 1222, and 1224, as shown in FIG. 12.

In sub-operation 1218 (FIG. 12), the database 210 may be queried for all note_cases records 310 and note_system records 312 whose note_id attribute matches the unique ID of the current note, in chronological order by insertion time. The reason for the chronological ordering is as discussed above in connection with FIG. 8.

In sub-operation 1220, all of the note_cases records 310 and note_systems records 312 whose note_id attribute matches the unique ID of the current note are returned in chronological order. In this example, sub-operation 1220 returns the previously added note_cases record 310 associated with the "Headache" medical case and the note_systems record 312 associated with the "Cardiology" body system just added in operation 1214. The result of operation 1220 will be a set of question IDs (for subjective tab 900) and prompt IDs (for objective tab 1000) ordered as they should appear in their respective tabs.

In sub-operation 1222 (FIG. 12), the set of question IDs resulting from operation 1220 may be sent to the database module 210 for retrieval of both the label attribute of the corresponding questions record 314 and the predetermined responses (answer records 320) associated with each question/prompt.

In sub-operation 1224 (FIG. 12), the labels and predetermined responses associated with each question/prompt requested in sub-operation 1222 are returned from the database module 210.

In operation 1226 (FIG. 12), the GUI module 220 displays the GUI screen 500 with the first GUI region (subjective tab 900) or the second GUI region (objective tab 1000) being visible, depending upon which of the two tabs 900 and 1000 is in focus.

Figure 13:
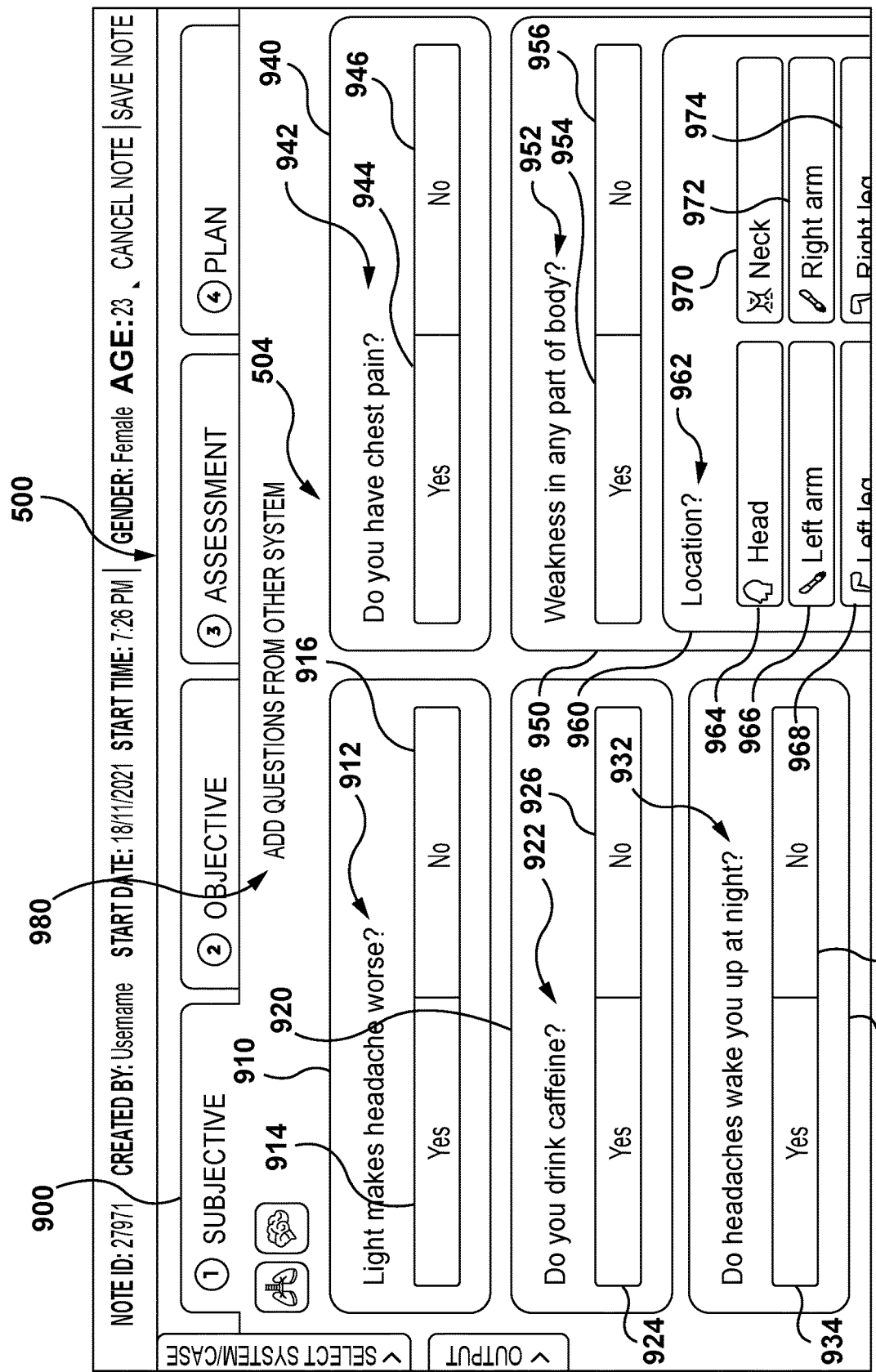
FIG. 13 is an example GUI screen that may be generated by the system of FIG. 1 on completion of the operation of FIG. 12.

FIG. 13 depicts the GUI screen 500 upon completion of operation 1200 of FIG. 12. As illustrated, the subjective tab 900 in the body 504 of GUI screen 500 has now been augmented with three additional question elements 940, 950, and 960 pertaining to the body system "Cardiology." The three new question elements supplement the previously populated question elements 910, 920, and 930 of FIG. 9. Like those previously populated question elements, each new question element 940, 950, and 960 includes the textual value of the "label" attribute of the associated questions record 314 (FIG. 3), displayed as textual indicator 942, 952, and 962, respectively, within a panel boundary. Each question element 940, 950, and 960 is also populated with a plurality of buttons (e.g., buttons 944 and 946 of panel 940; buttons 954 and 956 of question element 950; and buttons 964, 966, 968, 970, 972, and 974 of question element 960), also within the panel boundary.

It will be appreciated that, in FIG. 13, question element 960 is subordinate to, or dependent upon, question element 950. In this context, a dependent question element is one that seeks additional detail regarding an answer to the parent question element. In some embodiments, the dependent question element may be dynamically rendered only upon user selection of a particular one of the predetermined GUI response elements of the parent question element (e.g., question element 960 may appear only after "yes" button 954 of question element 950 has been selected by the user). In the present embodiment, the dependency of question element 960 upon question element 950 is represented by the graphical nesting of the panel of the former within the panel of the latter. It will be appreciated that, e.g., with the exception of the nesting, the rendering of a dependent question element may be substantially similar to the rendering of a parent question element.

Figure 14:
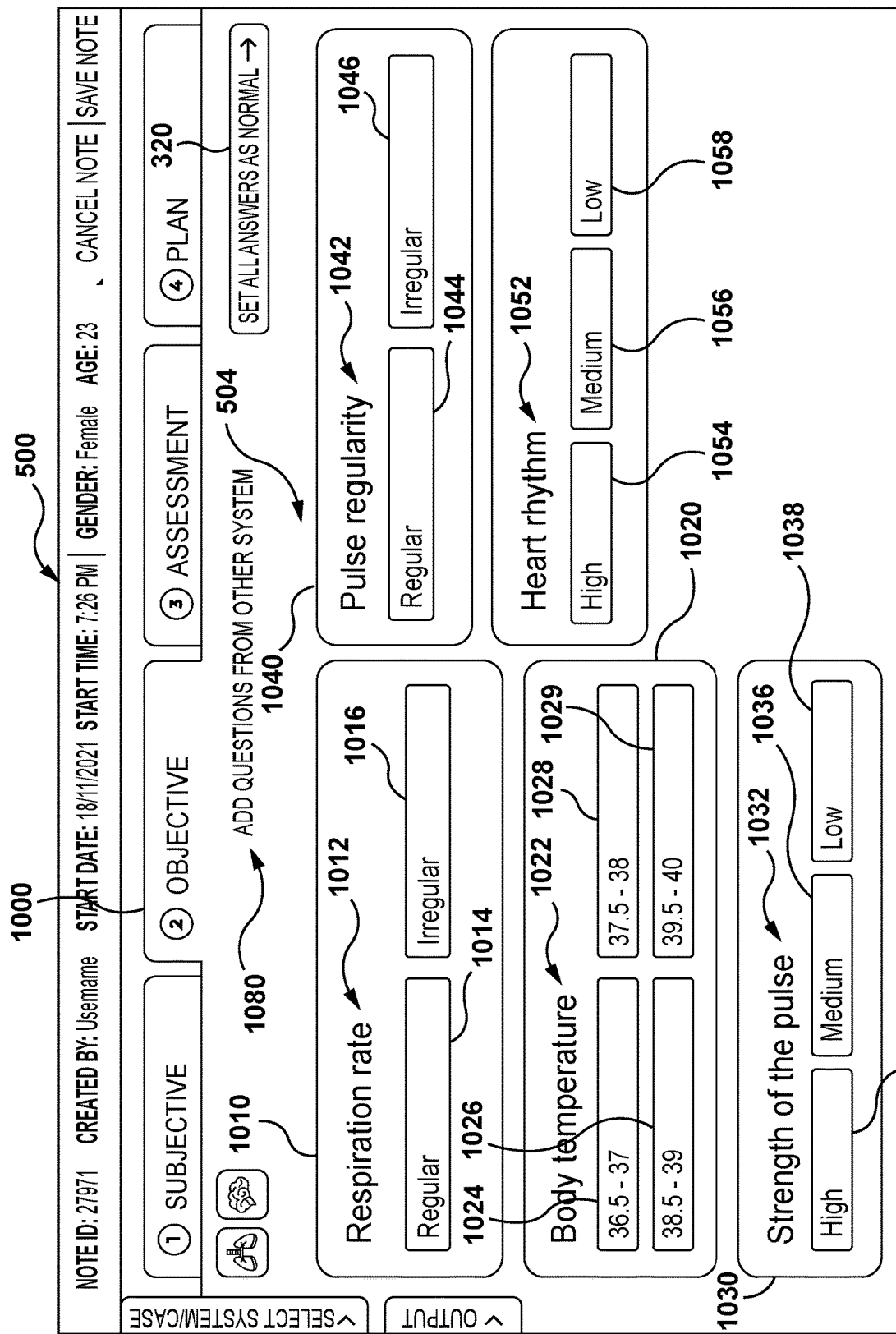
FIG. 14 is another example GUI screen that may be generated by the system of FIG. 1 on completion of the operation of FIG. 6.

To the extent that the objective tab 1000 is the current tab, the result of operation 1206 of FIG. 12 may be to display the GUI screen 500 with the populated objective tab 1000 visible as shown in FIG. 14.

FIG. 14 depicts the GUI screen 500 with the body 504 having been populated with three additional prompt elements 1030, 1040, and 1050. The three new prompt elements supplement the previously populated prompt elements 1010 and 1020 of FIG. 10. Like those previously populated prompt elements, each new prompt element 1030, 1040, and 1050 includes the textual value of the "label" attribute of the associated questions record 314 (FIG. 3), displayed as textual indicators 1032, 1042, and 1052, respectively, within a panel boundary. Each prompt element 1030, 1040, and 1050 is also populated with a plurality of user-selectable buttons (e.g., buttons 1034, 1036, and 1038 of prompt element 1030; buttons 1044 and 1046 of prompt element 1040; and buttons 1054, 1056, and 1058 of prompt element 1050), also within the panel boundary.

Figure 11:
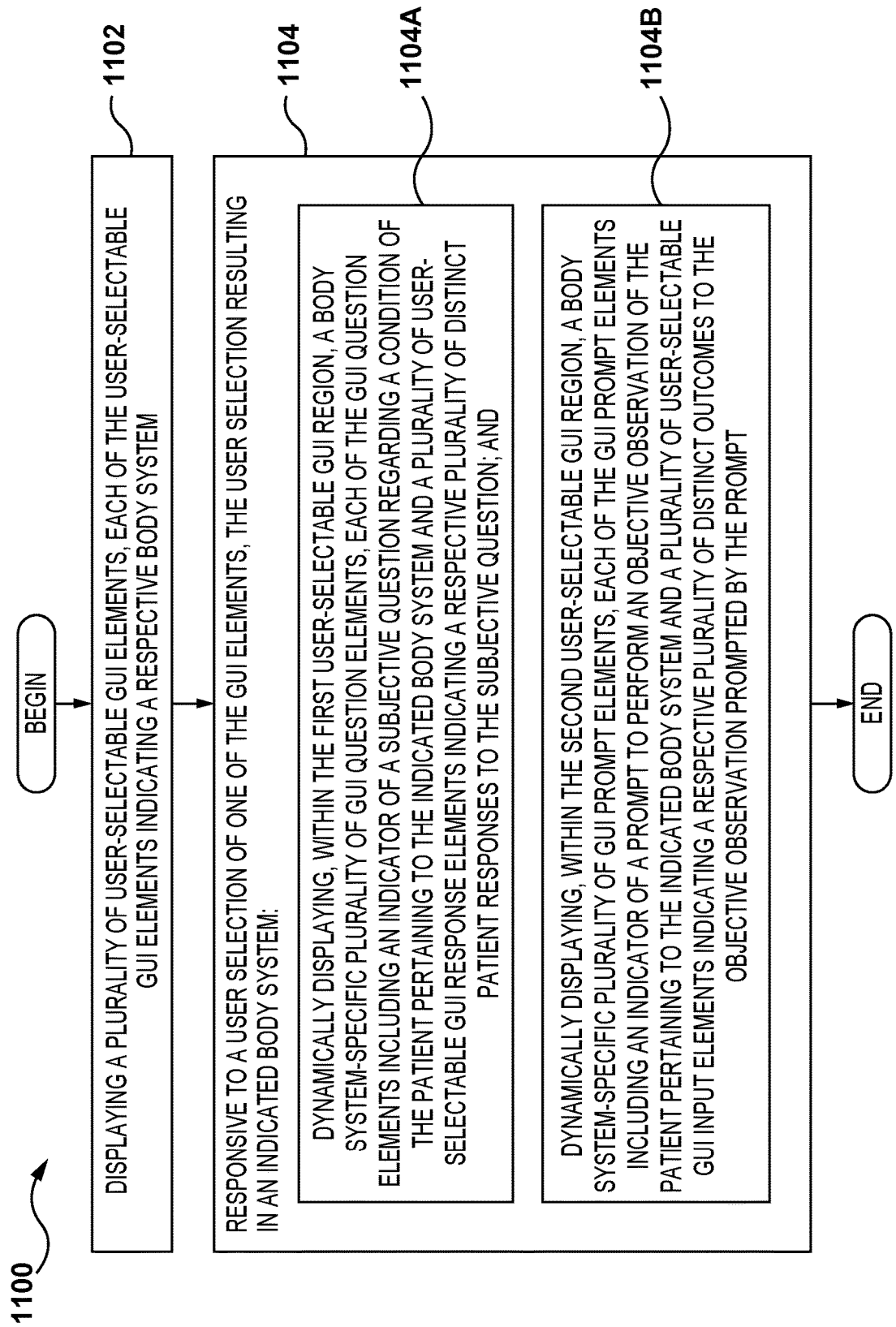
FIG. 11 is a flowchart illustrating further operation of the system of FIG. 1.
Figure 15:
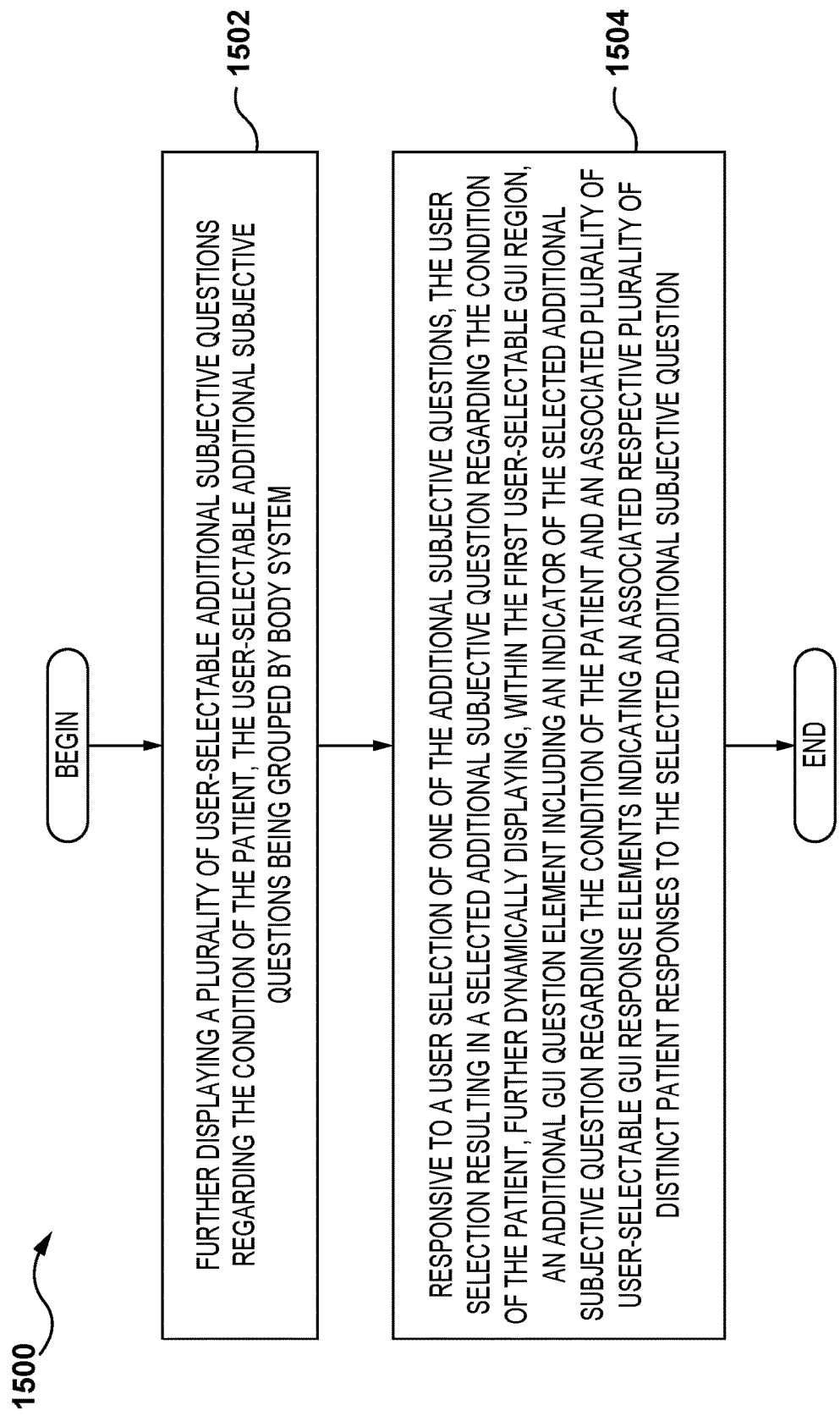
FIG. 15 is a flowchart depicting further operation of the system of FIG. 1.
Figure 16:
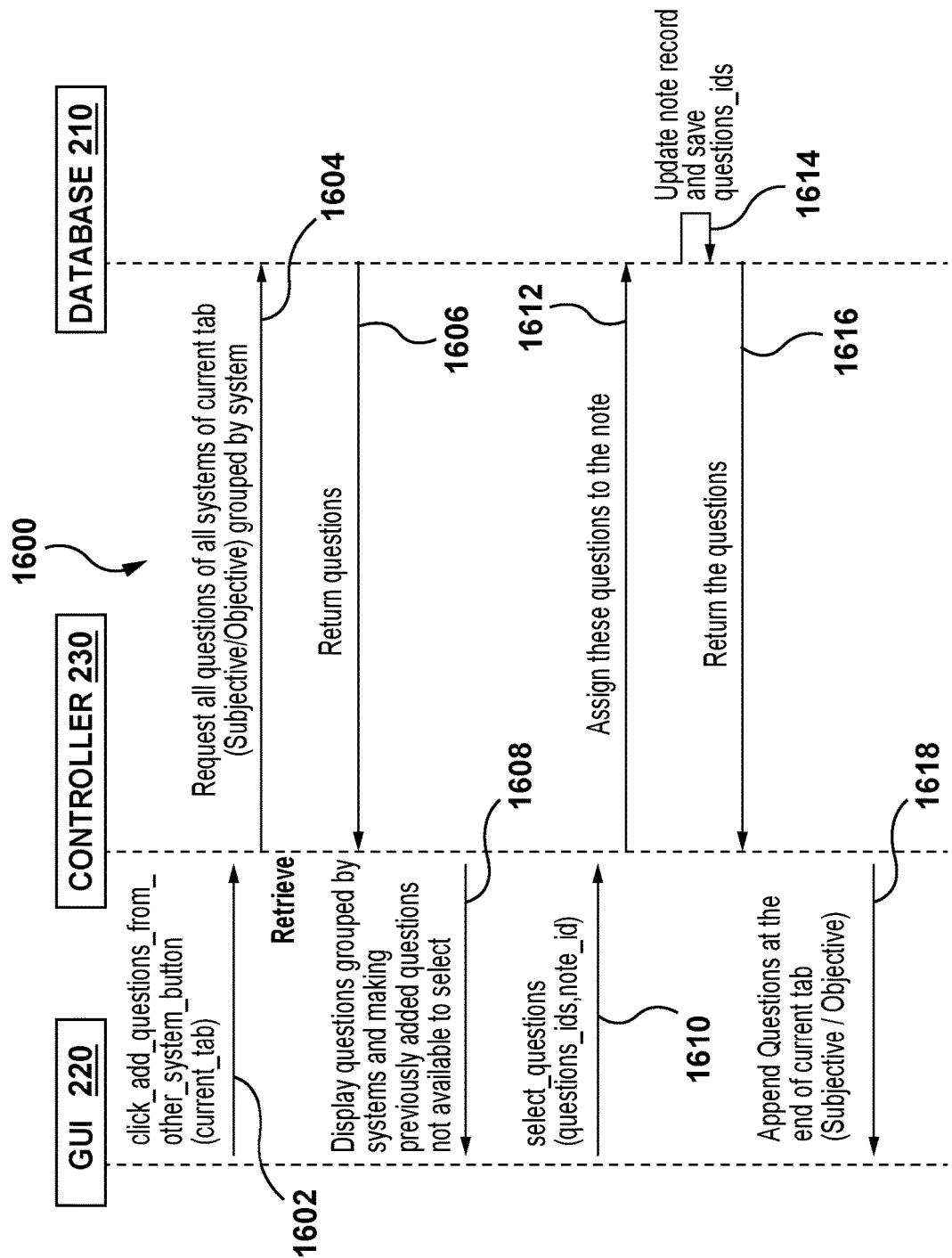
FIG. 16 is a sequence diagram depicting one implementation of the operation of FIG. 15.

It is possible that, during a medical appointment, the doctor 102 may wish to augment the GUI with one or more individually selected questions regarding a subjective condition of the patient without adding an entire "bundle" or set of questions relating to either a medical case (as described in FIG. 6) or a body system (as described in FIG. 11). FIGS. 15 and 16 depict such a scenario.

FIG. 15 is a flowchart of operation 1500 of system 100 for dynamically augmenting the first user-selectable GUI region with one or more individually chosen questions. To commence operation 1500, a user of system 100 may for example first select a GUI element, such as the "ADD QUESTION FROM OTHER SYSTEM" hyperlink 980 of FIG. 13.

In operation 1502 (FIG. 15), a plurality of user-selectable additional subjective questions regarding the condition of the patient, grouped by body system, is displayed. In one possible implementation, the GUI module 220 (FIG. 2) may initially present a pop-up dialog box (not depicted) with user-selectable GUI elements indicating each respective body system represented in the database 210 (which may be identified, e.g., by retrieving all systems records 308 from the database 210). Thereafter, selection of one of the GUI elements may cause all of the subjective questions for that body system to be displayed, each as a user-selectable element, in a body system-specific group. Questions already appearing in the subjective tab 900 may be rendered unselectable in the dialog box to avoid question duplication. The user may then be able to select one or more of the displayed subjective questions from the dialog box to identify the corresponding question element(s) to be added.

Responsive to the user selection of an additional subjective question in operation 1502, the first GUI region (subjective tab 900) may be augmented in operation 1504. In particular, and additional GUI question element is dynamically displayed within the subjective tab 900, e.g., after or below the last previously populated question element. The additional GUI question element includes an indicator of the selected additional subjective question and an associated plurality of GUI response elements indicating an associated respective plurality of distinct patient responses to the selected additional subjective question. In the present embodiment, operation 1504 may involve retrieving from the database module 210 the question record 314 whose the ID attribute matches the ID of the identified additional question and having a "Tab" attribute of "subjective." The additional question element may be rendered, e.g., as described above in connection with FIG. 9. Each of the GUI response elements may for example be based on a respective Answers record 320 associated with the relevant question record 314. The augmented subjective tab 900 may be immediately used by the doctor 102 to enter the patient's answer the dynamically added question.

In some embodiments, operation 1500 (FIG. 15) may be implemented by way of the interactions between the database 210, GUI 220, and controller 230 modules of application 125 (FIG. 2) as shown in the sequence diagram 1600 of FIG. 16.

In operation 1602 (FIG. 16), the GUI module 220 may invoke a method "click_add_questions_from_other_system_button" of the controller module 230, passing the current tab as a parameter. Operation 1602 may for example be triggered by user selection of the "ADD QUESTION FROM OTHER SYSTEM" hyperlink 980 of FIG. 13. In this scenario, the "current_tab" variable indicates subjective tab 900, i.e., the first GUI region.

At the controller module 230, the invoked method may trigger a database query of all the candidate questions records 314 for the current tab, i.e., whose associated "Tab" attribute (FIG. 3, record 314) is "subjective," grouped by system (operation 1604, FIG. 16). In some embodiments, this may entail a query for all the questions associated with each body system represented in database 210. These questions may be returned to the controller 230 in operation 1606 (FIG. 16).

In operation 1608 (FIG. 16), the returned questions may be displayed, e.g., in a pop-up dialog box (not expressly depicted), grouped by system. In the present embodiment, operation 1608 may include processing for avoiding redundancy in the questions of the subjective tab 900. In particular, redundancy of questions may for example be avoided by rendering unselectable in the dialog box (e.g., by pre-selecting and/or ghosting) any questions whose ID is already associated with the note record 304, e.g., via a case_questions record 316, via a system_questions record 318, or by being enumerated in the array of either the additional_subjective_questions attribute or the additional_objective_questions attribute of the note record 304.

In operation 1610 (FIG. 16), a user selection of one or more of the selectable questions displayed in operation 1608 may be received. In particular, a select_questions method may be invoked with two parameters: a first parameter comprising the unique question ID(s) of any question(s) selected in the dialog box and a second parameter comprising the unique ID of the current note.

In operations 1612 and 1614 (FIG. 16), the selected questions are assigned to the current note. In the present embodiment, this may be achieved by adding the unique IDs of the selected questions to the "additional_subjective_questions" array of the note record 304 representing the current note. Operation 1614 may also retrieve from the database module 210, for each selected question, the associated question record 314. The question record(s) 314 may be returned to the controller 230 in operation 1616.

In operation 1618 (FIG. 16), question elements corresponding to the question record(s) returned in operation 1616 may be added to the subjective tab 900.

Figure 17:
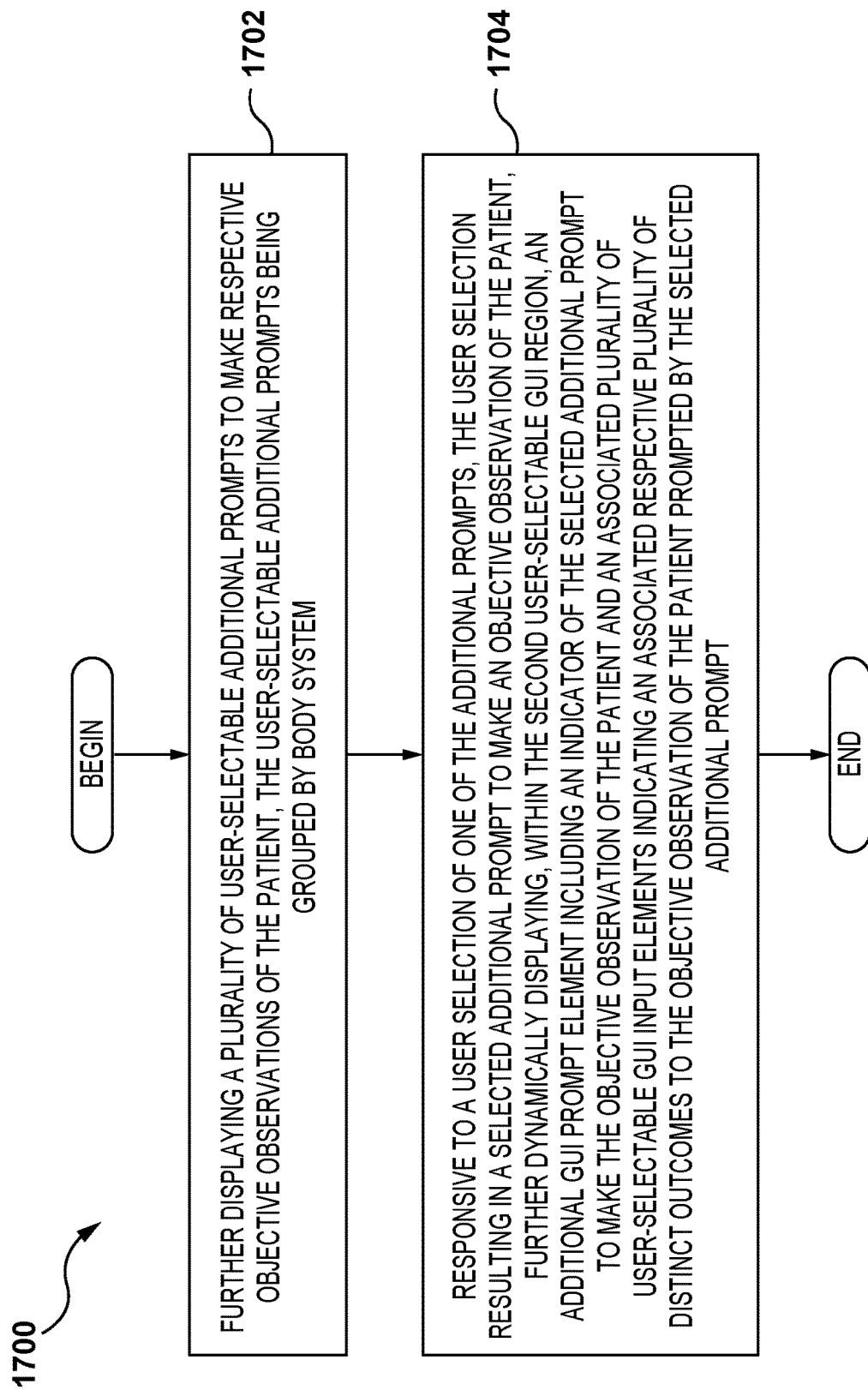
FIG. 17 is a flowchart depicting further operation of the system of FIG. 1.

It is further possible that, during the medical appointment, the doctor 102 may wish to add to the GUI one or more individually selected prompt elements prompting observations of the patient without adding an entire "bundle" or set of prompts relating to either a medical case (as described in connection with FIG. 6) or a body system (as described in connection with FIG. 11). FIG. 17 depicts such a scenario.

FIG. 17 is a flowchart of operation 1700 of system 100 for dynamically augmenting the second user-selectable GUI region with one or more individually chosen prompts. As will be appreciated, operation 1700 of FIG. 17 is similar to operation 1500 of FIG. 15 except that the GUI region that is dynamically augmented is the second GUI region (i.e., objective tab 1000) rather than the first GUI region (i.e., subjective tab 900) and that the augmentation is with one or more prompts rather than subjective questions. To commence operation 1700, a user of system 100 may for example first select a GUI element, such as the "ADD QUESTION FROM OTHER SYSTEM" hyperlink 1080 of FIG. 14.

In operation 1702 (FIG. 17), a plurality of user-selectable additional prompts to make respective objective medical observations of the patient, grouped by body system, is displayed. In one possible implementation, the GUI module 220 (FIG. 2) may initially present a pop-up dialog box with user-selectable GUI elements indicating each respective body system represented in the database 210 (which may be identified, e.g., by retrieving all systems records 308 from the database 210). Thereafter, selection of one of the body systems may cause all of the prompts for that body system to be displayed, each as a user-selectable element, in a body system-specific group. Prompts already appearing in the objective tab 1000 may be rendered unselectable in the dialog box to avoid prompt duplication. The user may then be able to select one or more of the displayed prompts from the dialog box to identify the corresponding prompt element(s) to be added.

Responsive to the user selection of an additional prompt in operation 1702, the second GUI region (objective tab 1000) may be augmented in operation 1704. In particular, an additional GUI prompt element is dynamically displayed within the objective tab 1000, e.g., after or below the last previously populated prompt element. The additional prompt element includes an indicator of the selected additional prompt and an associated plurality of GUI input elements indicating an associated respective plurality of distinct outcomes to the objective observation prompted by the additional prompt.

In the present embodiment, operation 1704 may involve retrieving from the database module 210 the question record 314 whose ID attribute matches the ID of the identified additional question and having a "Tab" attribute of "objective." Each of the GUI response elements may for example be based on a respective Answers record 320 associated with the relevant question record 314. The additional prompt element may be rendered, e.g., as described above in connection with FIG. 10. The augmented objective tab 1000 may be immediately used by the doctor 102 to perform the objective observation prompted by the dynamically added prompt.

As should now be appreciated, the above-described mechanisms permit a highly patient-specific and appointment-specific GUI for recording a medical appointment to be dynamically constructed with a minimum of user input actions. This is illustrated in the schematic diagram of FIG. 18.

Figure 18:
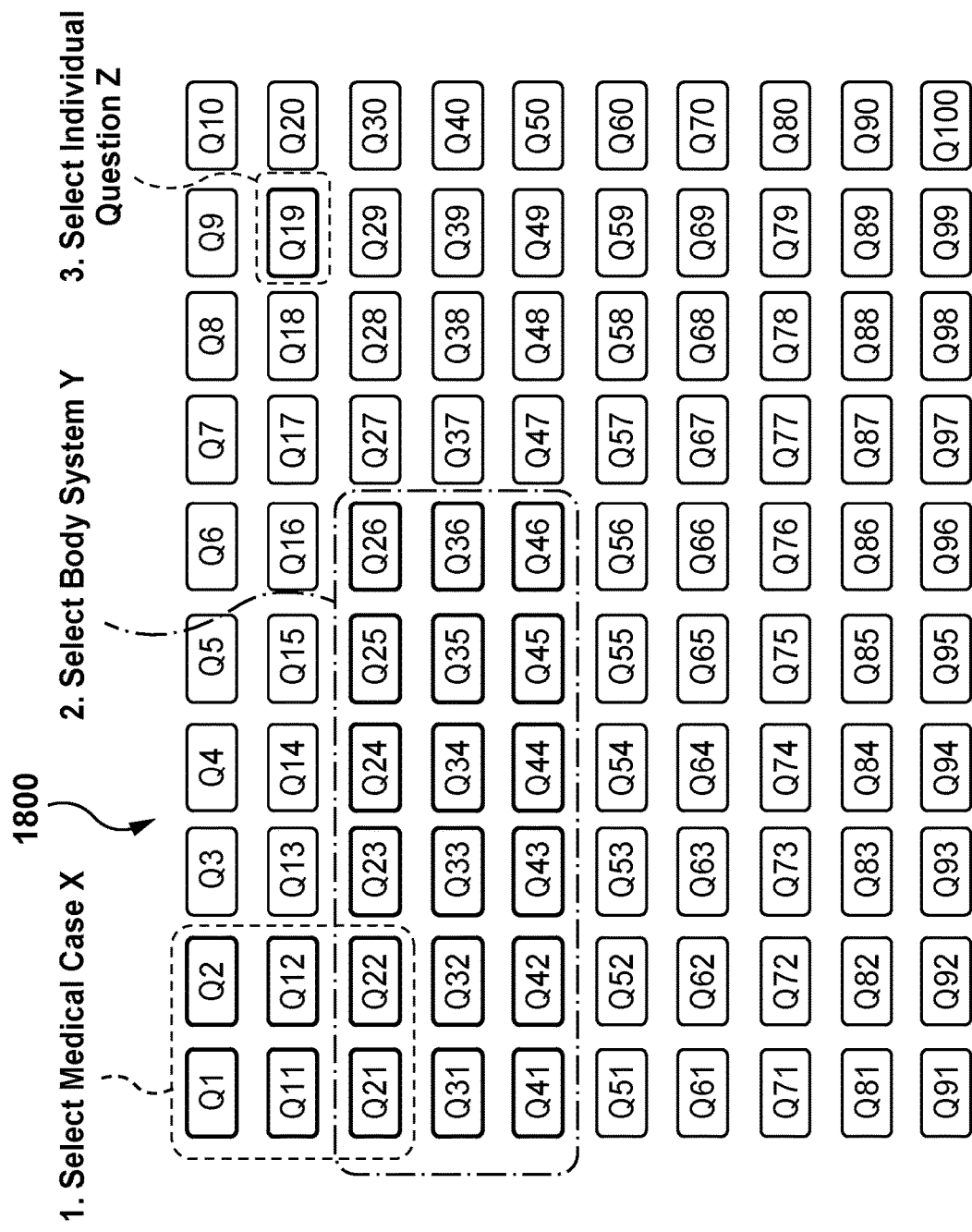
FIG. 18 is a schematic diagram depicting operation of the system of FIG. 1 that facilitates minimization of user input actions.

FIG. 18 is a schematic depiction of a pool 1800 of candidate subjective questions that may be stored in the database 210 of system 100. The example pool 1800 includes one hundred candidate questions Q1-Q100, each represented in FIG. 18 as a rounded rectangle. In this context, the term "candidate question" refers to a question that a doctor may wish to pose to a patient during a medical appointment, depending upon the needs of the patient.

In FIG. 18, questions with a bold border represent candidate questions that have been populated into a GUI region using system 100. FIG. 18 illustrates how a GUI can be quickly populated to contain a large number of relevant question elements (twenty-three in this example) using only three user input actions, which may be performed during a medical appointment with a patient.

In a first user input action, denoted in FIG. 18 with the text "1. Select Medical Case X," the doctor 102 may select one of the buttons 700 of FIG. 7 to specify a relevant medical case, which is denoted generically in FIG. 18 as case X. In this example, this selection triggers operation 600 of FIG. 6 for populating the GUI with six question elements based on six of the questions from pool 1800 that have been predesignated in database 210 as pertaining to medical case X: Q1, Q2, Q11, Q12, Q21, and Q22.

In a second user input action, denoted in FIG. 18 with the text "2. Select Body System Y," the doctor 102 may select one of the buttons 750 of FIG. 7 to specify a relevant body system, which is denoted generically in FIG. 18 as body system Y. In this example, this selection triggers operation 600 of FIG. 6 for augmenting the GUI with 16 question elements based on the 16 questions from pool 1800 that have been predesignated in database 210 as pertaining to body system Y: Q23, Q24, Q25, Q26, Q31, Q32, Q33, Q34, Q35, Q36, Q41, Q42, Q43, Q44, Q45, and Q46. Notably, questions Q21 and Q22, which have also been predesignated as relevant to body system Y, are not populated into the GUI as a result of the second user input action. The reason is that questions Q21 and Q22 have already been populated into the GUI responsive to the first user action.

In a third user input action, denoted in FIG. 18 with the text "3. Select Individual Question Z," the doctor 102 may select an individual subjective question, Q19, to be added to the GUI. In this example, this selection triggers operation 1500 of FIG. 15 for augmenting the GUI with a question element based on the selected question.

In the result, three user input actions have generated a highly patient-specific and appointment-specific GUI containing twenty-three questions and associated predetermined responses that can be immediately used to facilitate generating a record of the medical appointment. It will be appreciated that a similar approach may be taken for quickly populating a second GUI region with prompts regarding objective observations of the patient from a pool of prompts analogous to pool 1800 of FIG. 18.

Various alternative embodiments are possible.

In at least some embodiments described above, the system displays a GUI with first and second independently user-selectable GUI regions that are tabs. In alternative embodiments, the GUI regions need not be tabs. For example, in some embodiments, the GUI regions could be window panes, which may be overlapping window panes. In some embodiments, the GUI regions are not user-selectable and/or are not overlapping, although this may sacrifice efficiency, e.g., in GUI real-estate utilization.

Although the system 100 is described above as being implemented in part as a web-based application 125, this is not strictly required. Alternative embodiment systems may for example use a client-server model with a dedicated client application at the local computing device. Alternatively, the system could be implemented entirely on a single computing device.

The local computing device is not strictly required to have a touchscreen 114. However, a touchscreen may be convenient, e.g., to avoid possibly awkward or error-prone interactions involving a mouse, trackball, or stylus.

The GUI elements used to specify medical cases and body systems need not necessarily be buttons and need not necessarily be displayed for selection on one or more expandable tabs. Other user-selectable GUI elements may be used for this purpose.

The methods and systems described herein may be deployed in part or in whole through a machine that executes computer software, program codes, and/or instructions on a processor. The processor may be part of a server, cloud server, client, network infrastructure, mobile computing platform, stationary computing platform, or other computing platform. A processor may be any kind of computational or processing device capable of executing program instructions, codes, binary instructions, and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. By way of implementation, methods, program codes, program instructions and the like described herein may be implemented in one or more threads. The processor may include memory that stores methods, codes, instructions, and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of an optical storage medium such as CD-ROM or DVD, memory, hard disk, flash drive, RAM, ROM, cache, and the like. The methods and/or processes described above, and operations thereof, may be realized in hardware, software, firmware, or a combination of any of these.

What is claimed is:

1. A computer-implemented method comprising:
   displaying, by a computing device, a graphical user interface (GUI) screen having a body;
   displaying, by the computing device, at least one expandable tab in a collapsed state within the GUI screen;
   responsive to a user selection of the at least one expandable tab in the collapsed state, expanding the at least one expandable tab to an expanded state and presenting on the at least one expandable tab a first plurality of user-selectable GUI elements and a second plurality of user-selectable GUI elements, each of the first plurality of user-selectable GUI elements indicating a respective type of medical case, each of the second plurality of user-selectable GUI elements indicating a respective body system, wherein the at least one expandable tab, when in an expanded state, partially overlays the body of the GUI screen;
   dynamically creating, in the body of the GUI screen, a patient-specific GUI by:
      responsive to a user selection of one of the first plurality of GUI elements presented on the at least one expandable tab, the user selection resulting in an indicated type of medical case:
         dynamically displaying, by the computing device, within a first user-selectable GUI region of the body of the GUI screen, a medical case-specific plurality of GUI question elements, each of the GUI question elements including:
            an indicator of a subjective question regarding a condition of a patient presenting with the indicated type of medical case; and
            a plurality of user-selectable GUI response elements indicating a respective plurality of distinct patient responses to the subjective question; and
         dynamically displaying, by the computing device, within a second user-selectable GUI region of the body of the GUI screen, the second user-selectable GUI region being independently user-selectable from the first user-selectable GUI region, a medical case-specific plurality of GUI prompt elements, each of the GUI prompt elements including:
            an indicator of a prompt to perform an objective observation of the patient presenting with the indicated type of medical case; and
            a plurality of user-selectable GUI input elements indicating a respective plurality of distinct outcomes to the prompted objective observation; and
      responsive to a user selection of one of the second plurality of GUI elements presented on the at least one expandable tab, the user selection resulting in an indicated body system:
         further dynamically displaying, by the computing device, within the first user-selectable GUI region displaying the medical case-specific plurality of GUI question elements, a body system-specific plurality of further GUI question elements, each of the further GUI question elements including:
            an indicator of a further subjective question regarding a condition of the patient pertaining to the indicated body system; and
            a further plurality of user-selectable GUI response elements indicating a respective plurality of distinct patient responses to the further subjective question; and
         further dynamically displaying, by the computing device, within the second user-selectable GUI region displaying the medical case-specific plurality of GUI prompt elements, a body system-specific plurality of further GUI prompt elements, each of the further GUI prompt elements including:
            an indicator of a further prompt to perform an objective observation of the patient pertaining to the indicated body system; and
            a further plurality of user-selectable GUI input elements indicating a respective further plurality of distinct outcomes to the objective observation prompted by the further prompt.

2. The computer-implemented method of claim 1 wherein the at least one expandable tab, in the collapsed state, is displayed at a side of the GUI screen.

3. The computer-implemented method of claim 2 wherein the further dynamically displaying of the body system-specific plurality of further GUI question elements includes removing at least one redundant question element as between the body system-specific plurality of further GUI question elements and the medical case-specific plurality of GUI question elements.

4. The computer-implemented method of claim 1 further comprising:
further displaying, by the computing device, a plurality of user-selectable additional subjective questions regarding the condition of the patient, the user-selectable additional subjective questions being grouped by body system;
responsive to a user selection of one of the additional subjective questions, the user selection resulting in a selected additional subjective question regarding the condition of the patient, further dynamically displaying, by the computing device, within the first user-selectable GUI region, an additional GUI question element including:
an indicator of the selected additional subjective question regarding the condition of the patient; and
an associated plurality of user-selectable GUI response elements indicating an associated respective plurality of distinct patient responses to the selected additional subjective question.

5. The computer-implemented method of claim 1 further comprising:
further displaying, by the computing device, a plurality of user-selectable additional prompts to make respective objective observations of the patient, the user-selectable additional prompts being grouped by body system;
responsive to a user selection of one of the additional prompts, the user selection resulting in a selected additional prompt to make an objective observation of the patient, further dynamically displaying, by the computing device, within the second user-selectable GUI region, an additional GUI prompt element including:
an indicator of the selected additional prompt to make the objective observation of the patient; and
an associated plurality of user-selectable GUI input elements indicating an associated respective plurality of distinct outcomes to the objective observation of the patient prompted by the selected additional prompt.

6. The computer-implemented method of claim 1 further comprising receiving a user selection of one of the first user-selectable GUI region and the second user-selectable GUI region and, responsive thereto, causing, by the computing device, the selected one of the first user-selectable GUI region and the second user-selectable GUI region to at least partially overlay the other of the first user-selectable GUI region and the second user-selectable GUI region.

7. The computer-implemented method of claim 1 wherein the at least one expandable tab containing the plurality of user-selectable GUI elements indicating respective types of medical cases is vertically oriented.

8. A system comprising:
a computing device including:
at least one processor; and
non-transitory memory, communicatively coupled to the at least one processor, storing instructions that, upon execution by the at least one processor, cause the computing device to:
display a graphical user interface (GUI) screen having a body;
display an expandable tab in a collapsed state within the GUI screen;
responsive to a user selection of the expandable tab in the collapsed state, expand the expandable tab to an expanded state and present on the expandable tab a first plurality of user-selectable GUI elements and a second plurality of user-selectable GUI elements, each of the first plurality of user-selectable GUI elements indicating a respective type of medical case, each of the second plurality of user-selectable GUI elements indicating a respective body system, wherein the expandable tab, when in an expanded state, partially overlays the body of the GUI screen;
dynamically create, in the body of the GUI screen, a patient-specific GUI by:
responsive to a user selection of one of the GUI elements presented on the expandable tab, the user selection resulting in an indicated type of medical case:
dynamically displaying, within a first user-selectable GUI region of the body of the GUI screen, a medical case-specific plurality of GUI question elements, each of the GUI question elements including:
an indicator of a subjective question regarding a condition of a patient presenting with the indicated type of medical case; and
a plurality of user-selectable GUI response elements indicating a respective plurality of distinct patient responses to the subjective question; and
dynamically displaying, within a second user-selectable GUI region of the body of the GUI screen, the second user-selectable GUI region being independently user-selectable from the first user-selectable GUI region, a medical case-specific plurality of GUI prompt elements, each of the GUI prompt elements including:
an indicator of a prompt to perform an objective observation of the patient presenting with the indicated type of medical case; and
a plurality of user-selectable GUI input elements indicating a respective plurality of distinct outcomes to the prompted objective observation; and
responsive to a user selection of one of the second plurality of GUI elements presented on the expandable tab, the user selection resulting in an indicated body system:
further dynamically displaying, within the first user-selectable GUI region displaying the medical case-specific plurality of GUI question elements, a body system-specific plurality of further GUI question elements, each of the further GUI question elements including:

an indicator of a further subjective question regarding a condition of the patient pertaining to the indicated body system; and
a further plurality of user-selectable GUI response elements indicating a respective plurality of distinct patient responses to the further subjective question; and
further dynamically displaying, within the second user-selectable GUI region displaying the medical case-specific plurality of GUI prompt elements, a body system-specific plurality of further GUI prompt elements, each of the further GUI prompt elements including:
an indicator of a further prompt to perform an objective observation of the patient pertaining to the indicated body system; and
a further plurality of user-selectable GUI input elements indicating a respective further plurality of distinct outcomes to the objective observation prompted by the further prompt.

9. The system of claim 8 wherein the expandable tab, in the collapsed state, is displayed at a side of the GUI screen.

10. The system of claim 9 wherein the further dynamically displaying of the body system-specific plurality of further GUI question elements includes removing at least one redundant question element as between the body system-specific plurality of further GUI question elements and the medical case-specific plurality of GUI question elements.

11. The system of claim 8 wherein the instructions further cause the computing device to:
further display a plurality of user-selectable additional subjective questions regarding the condition of the patient, the user-selectable additional subjective questions being grouped by body system;
responsive to a user selection of one of the additional subjective questions, the user selection resulting in a selected additional subjective question regarding the condition of the patient, further dynamically display, within the first user-selectable GUI region, an additional GUI question element including:
an indicator of the selected additional subjective question regarding the condition of the patient; and
an associated plurality of user-selectable GUI response elements indicating an associated respective plurality of distinct patient responses to the selected additional subjective question.

12. The system of claim 8 wherein the instructions further cause the computing device to:
further display a plurality of user-selectable additional prompts to make respective objective observations of the patient, the user-selectable additional prompts being grouped by body system;
responsive to a user selection of one of the additional prompts, the user selection resulting in a selected additional prompt to make an objective observation of the patient, further dynamically display, within the second user-selectable GUI region, an additional GUI prompt element including:
an indicator of the selected additional prompt to make the objective observation of the patient; and
an associated plurality of user-selectable GUI input elements indicating an associated respective plurality of distinct outcomes to the objective observation of the patient prompted by the selected additional prompt.

13. The system of claim 8 wherein the instructions further cause the computing device to receive a user selection of one of the first user-selectable GUI region and the second user-selectable GUI region and, responsive thereto, cause the selected one of the first user-selectable GUI region and the second user-selectable GUI region to at least partially overlay the other of the first user-selectable GUI region and the second user-selectable GUI region.

14. The system of claim 8 wherein the expandable tab containing the plurality of user-selectable GUI elements indicating respective types of medical cases is vertically oriented.

15. A non-transitory machine-readable medium storing instructions that, when executed by one or more processors of a computing device, cause the computing device to:
display, on a display of a computing device, a graphical user interface (GUI) screen having a body;
display, on the display of the computing device, an expandable tab in a collapsed state within the GUI screen;
responsive to a user selection of the expandable tab in the collapsed state, expand the expandable tab to an expanded state and present on the expandable tab a first plurality of GUI elements and a second plurality of user-selectable GUI elements, each of the user-selectable GUI elements indicating a respective type of medical case, each of the second plurality of user-selectable GUI elements indicating a respective body system, wherein the expandable tab, when in an expanded state, partially overlays the body of the GUI screen;
dynamically create, in the body of the GUI screen, a patient-specific GUI by:
responsive to a user selection of one of the first plurality of GUI elements presented on the expandable tab, the user selection resulting in an indicated type of medical case:
dynamically displaying, on the display of the computing device, within a first user-selectable GUI region of the body of the GUI screen, a medical case-specific plurality of GUI question elements, each of the GUI question elements including:
an indicator of a subjective question regarding a condition of a patient presenting with the indicated type of medical case; and
a plurality of user-selectable GUI response elements indicating a respective plurality of distinct patient responses to the subjective question; and
dynamically displaying, on the display of the computing device, within a second user-selectable GUI region of the body of the GUI screen, the second user-selectable GUI region being independently user-selectable from the first user-selectable GUI region, a medical case-specific plurality of GUI prompt elements, each of the GUI prompt elements including:
an indicator of a prompt to perform an objective observation of the patient presenting with the indicated type of medical case; and
a plurality of user-selectable GUI input elements indicating a respective plurality of distinct outcomes to the prompted objective observation and;

responsive to a user selection of one of the second plurality of GUI elements presented on the expandable tab, the user selection resulting in an indicated body system:
  further dynamically displaying, by the computing device, within the first user-selectable GUI region displaying the medical case-specific plurality of GUI question elements, a body system-specific plurality of further GUI question elements, each of the further GUI question elements including:
    an indicator of a further subjective question regarding a condition of the patient pertaining to the indicated body system; and
    a further plurality of user-selectable GUI response elements indicating a respective plurality of distinct patient responses to the further subjective question; and
  further dynamically displaying, by the computing device, within the second user-selectable GUI region displaying the medical case-specific plurality of GUI prompt elements, a body system-specific plurality of further GUI prompt elements, each of the further GUI prompt elements including:
    an indicator of a further prompt to perform an objective observation of the patient pertaining to the indicated body system; and
    a further plurality of user-selectable GUI input elements indicating a respective further plurality of distinct outcomes to the objective observation prompted by the further prompt.

16. The non-transitory machine-readable medium of claim 15 wherein the expandable tab, in the collapsed state, is displayed at a side of the GUI screen.

17. The non-transitory machine-readable medium of claim 16 wherein the further dynamically displaying of the body system-specific plurality of further GUI question elements includes removing at least one redundant question element as between the body system-specific plurality of further GUI question elements and the medical case-specific plurality of GUI question elements.

18. The non-transitory machine-readable medium of claim 15 wherein the instructions further cause the computing device to:
  further display, on the display of the computing device, a plurality of user-selectable additional subjective questions regarding the condition of the patient, the user-selectable additional subjective questions being grouped by body system;
  responsive to a user selection of one of the additional subjective questions, the user selection resulting in a selected additional subjective question regarding the condition of the patient, further dynamically display, on the display of the computing device, within the first user-selectable GUI region, an additional GUI question element including:
    an indicator of the selected additional subjective question regarding the condition of the patient; and
    an associated plurality of user-selectable GUI response elements indicating an associated respective plurality of distinct patient responses to the selected additional subjective question.

19. The non-transitory machine-readable medium of claim 15 wherein the instructions further cause the computing device to:
  further display, on the display of the computing device, a plurality of user-selectable additional prompts to make respective objective observations of the patient, the user-selectable additional prompts being grouped by body system;
  responsive to a user selection of one of the additional prompts, the user selection resulting in a selected additional prompt to make an objective observation of the patient, further dynamically display, on the display of the computing device, within the second user-selectable GUI region, an additional GUI prompt element including:
    an indicator of the selected additional prompt to make the objective observation of the patient; and
    an associated plurality of user-selectable GUI input elements indicating an associated respective plurality of distinct outcomes to the objective observation of the patient prompted by the selected additional prompt.

20. The non-transitory machine-readable medium of claim 15 wherein the instructions further cause the computing device to receive a user selection of one of the first user-selectable GUI region and the second user-selectable GUI region and, responsive thereto, cause the selected one of the first user-selectable GUI region and the second user-selectable GUI region to at least partially overlay the other of the first user-selectable GUI region and the second user-selectable GUI region.

\* \* \* \* \*